United States Patent
Gao et al.

(10) Patent No.: US 12,187,697 B2
(45) Date of Patent: Jan. 7, 2025

(54) DIOXIN DERIVATIVES, PREPARATION METHODS THEREOF, ELECTRON TRANSPORT LAYERS, OLED DEVICES AND DISPLAY PANELS

(71) Applicant: BOE Technology Group Co., Ltd., Beijing (CN)

(72) Inventors: Rongrong Gao, Beijing (CN); Dongxu Zhang, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 659 days.

(21) Appl. No.: 17/359,457

(22) Filed: Jun. 25, 2021

(65) Prior Publication Data
US 2022/0073491 A1    Mar. 10, 2022

(30) Foreign Application Priority Data
Sep. 7, 2020   (CN) .......................... 202010931127.0

(51) Int. Cl.
| C07D 319/24 | (2006.01) |
| H10K 50/11 | (2023.01) |
| H10K 50/16 | (2023.01) |
| H10K 85/60 | (2023.01) |
| H10K 101/40 | (2023.01) |

(52) U.S. Cl.
CPC ......... *C07D 319/24* (2013.01); *H10K 85/624* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/16* (2023.02); *H10K 2101/40* (2023.02)

(58) Field of Classification Search
CPC ... H10K 50/16; H10K 85/654; H10K 85/6574
See application file for complete search history.

(56) References Cited

U.S. PATENT DOCUMENTS

| 10,756,277 B2 * | 8/2020 | Choi | .................. C07D 491/056 |
| 2017/0170406 A1 | 6/2017 | Choi et al. | |

FOREIGN PATENT DOCUMENTS

| CN | 106458961 A | 2/2017 | |
| CN | 107089990 A | 8/2017 | |
| CN | 107337680 A | 11/2017 | |
| CN | 109535168 A | 3/2019 | |
| CN | 110494430 A | 11/2019 | |
| CN | 110741002 A | 1/2020 | |
| CN | 110963989 A | 4/2020 | |
| CN | 111592527 A | 8/2020 | |
| KR | 20160060572 A * | 5/2016 | ............. C09K 11/06 |
| NO | 2017023126 A1 | 2/2017 | |
| WO | WO-2015156580 A2 * | 10/2015 | ........... C07D 319/24 |

OTHER PUBLICATIONS

CN202010931127.0 First Office Action.
CN202010931127.0 Second Office Action.
Gao, Y., et al. "Synthesis of electroluminescence combinations containing 1, 3, 4-oxadiazole and triazine Units." Chemical Research and Application 17.3 (2005): 366.

* cited by examiner

*Primary Examiner* — Vu A Nguyen
(74) *Attorney, Agent, or Firm* — IPro, PLLC

(57) ABSTRACT

The present application provides a dioxin derivative, a preparation method thereof, an electron transport layer, an OLED device and a display panel. The dioxin derivative has a formula of

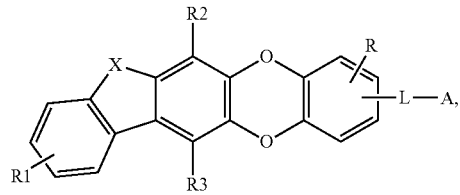

where X is O, S or NR; L represents a direct bond, or L is a substituted or unsubstituted $C_6$-$C_{60}$ arylene, or L is a $C_2$-$C_{60}$ heteroaryl including a first heteroatom; A has a formula of

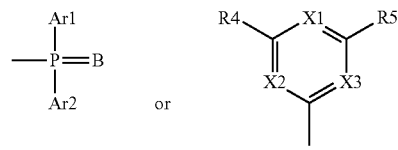

Ar1 and Ar2 independently are substituted or unsubstituted aryl, phenyl, biphenyl, or heterocyclyl comprising a second heteroatom, B is O, S or Se, X1, X2 and X3 independently are C or N, and at least one of X1, X2 or X3 is N, R4 and R5 independently are $C_5$-$C_{30}$ aromatic or heteroaromatic group ring.

5 Claims, 5 Drawing Sheets

Figure 1A:
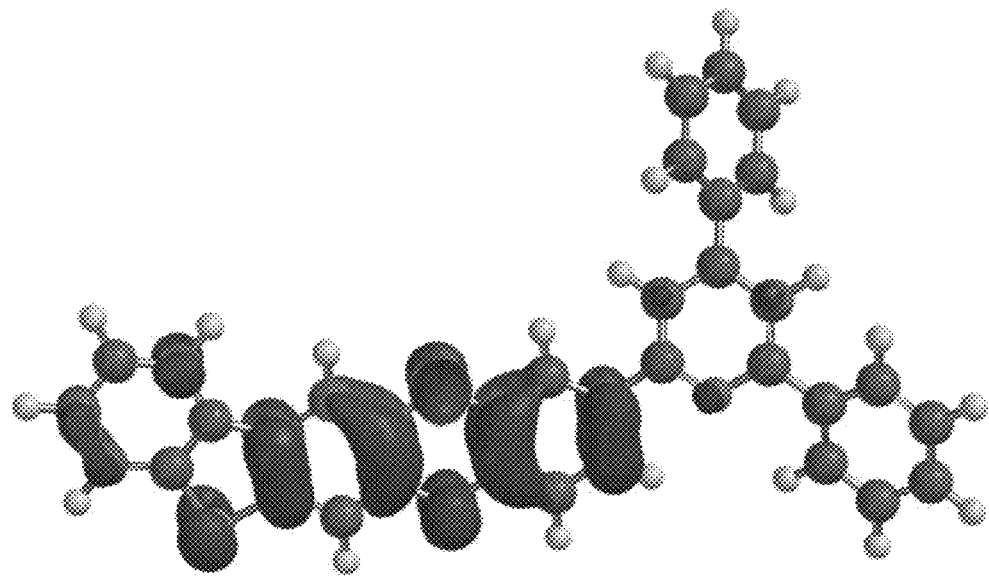

DIOXIN DERIVATIVES, PREPARATION METHODS THEREOF, ELECTRON TRANSPORT LAYERS, OLED DEVICES AND DISPLAY PANELS

CROSS REFERENCE TO RELATED APPLICATIONS

This application claims priority to Chinese Patent Application No. 202010931127.0, titled "DIOXIN DERIVATIVES, PREPARATION METHODS AND APPLICATIONS THEREOF", filed on Sep. 7, 2020, the contents of all of which are incorporated herein by reference.

TECHNICAL FIELD

This application relates to the field of material technology, and in particular, to a dioxin derivative and a preparation method thereof, an electron transport layer, an OLED device and a display panel.

BACKGROUND

OLED (Organic Light-Emitting Diode) is a display technology emerged in recent years. It has advantages of being self-luminous, low power consumption, vivid colors, larger viewing angles, and can be made into flexible products. An OLED is composed of multiple layered structures. Various functional layers and interaction at functional layer interfaces directly or indirectly affect injection, transport, and diffusion of carriers inside the devices, as well as formation, diffusion, and quenching of excitons. Thus, functional layer materials of OLEDs play a decisive role in device performances (such as current density, luminance, luminous efficiency, stability, etc.). As a core material of OLEDs, organic electron transport materials in the organic functional layer of OLEDs have an important influence on performance and stability of OLEDs.

SUMMARY

In an aspect of this application, a dioxin derivative is provided of a formula:

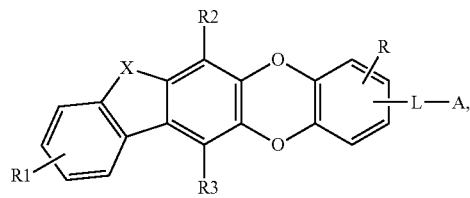

where X is O, S or NR; R, R1, R2 and R3 independently are hydrogen, deuterium, halogen, cyano, nitro, $C_1$-$C_{40}$ alkyl, $C_2$-$C_{40}$ alkenyl, $C_2$-$C_{40}$ alkynyl, $C_3$-$C_{40}$ cycloalkyl, $C_3$-$C_{40}$ heterocycloalkyl, $C_6$-$C_{60}$ aryl, $C_5$-$C_{60}$ heteroaryl, $C_1$-$C_{40}$ alkoxy, $C_6$-$C_{60}$ aryloxy, $C_3$-$C_{40}$ alkylsilyl, $C_6$-$C_{60}$ arylsilyl, $C_1$-$C_{40}$ alkylboryl, $C_6$-$C_{60}$ arylboryl, $C_6$-$C_{60}$ arylphosphonoyl, $C_6$-$C_{60}$ mono- or di-arylphosphanyl, or $C_6$-$C_{60}$ arylamino; L represents a direct bond, or L is a substituted or unsubstituted $C_6$-$C_{60}$ arylene, or L is a $C_2$-$C_{60}$ heteroaryl including a first heteroatom; A has a formula of

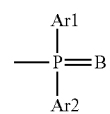

or

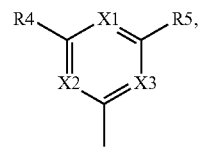

where Ar1 and Ar2 independently are substituted or unsubstituted aryl, phenyl, biphenyl or heterocyclyl including a second heteroatom, B is O, S or Se; X1, X2 and X3 independently are C or N, and at least one of X1, X2 or X3 is N; R4 and R5 independently are $C_5$-$C_{30}$ aromatic, or heteroaromatic group ring.

According to an embodiment of the present application, at least one of R4 or R5 is substituted by R3.

According to an embodiment of the present application, the first heteroatom is at least one of N, O, S or Si.

According to an embodiment of the present application, the second heteroatom is at least one of N, O or S.

According to an embodiment of the present application, at least one of R4 or R5 includes a third heteroatom, and the third heteroatom is at least one of N, S or B.

According to an embodiment of the present application, a first group and a second group bonded to a same third heteroatom are bonded with each other through a single bond, or the first group and the second group are bridged with B(R3), C(R3)$_2$, Si(R3)$_2$, C=O, C=N(R3), C=C(R3)$_2$, O, S, S=O, SO$_2$, N(R3), P(R3) or P(=O)R3.

According to an embodiment of the present application, the first group and the second group independently are phenyl, aryl or alkyl.

According to an embodiment of the present application, the dioxin derivative is one of the followings:
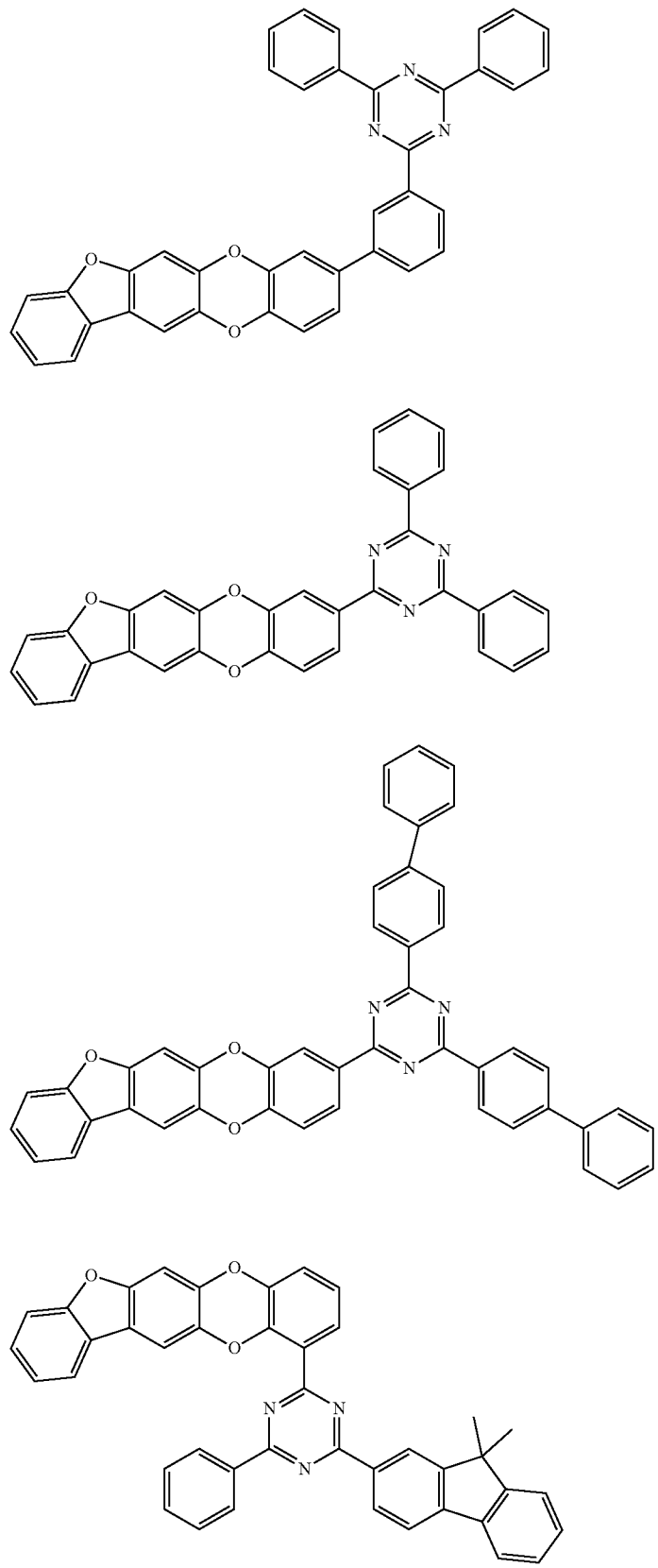

-continued
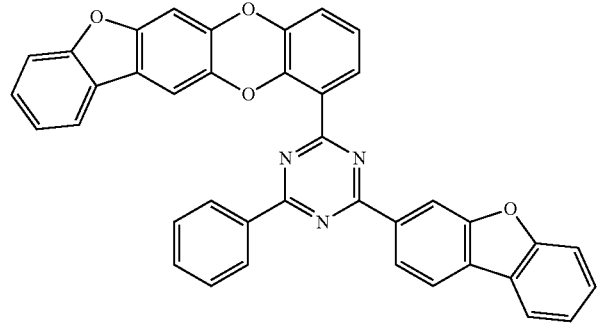
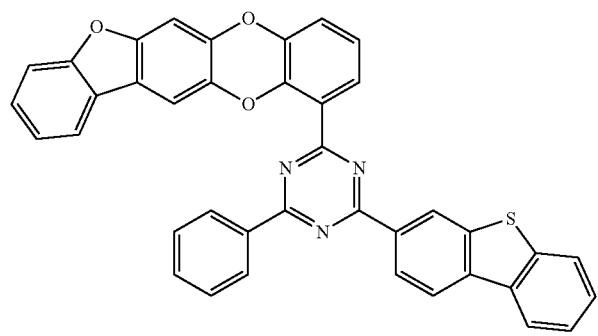
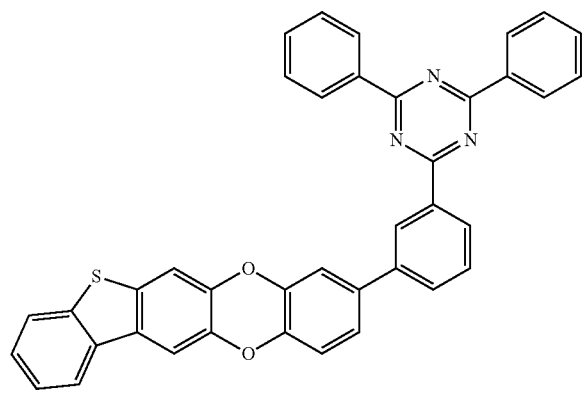
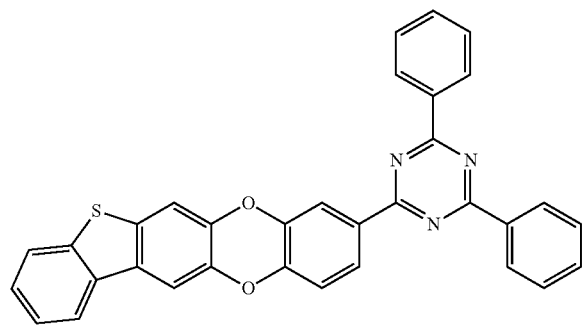

-continued
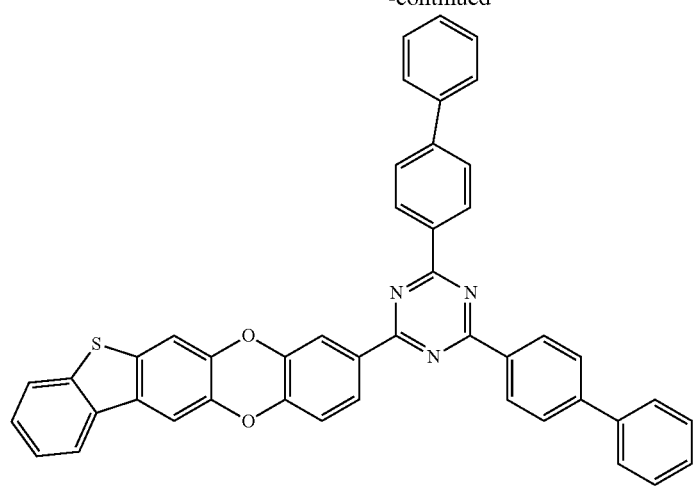
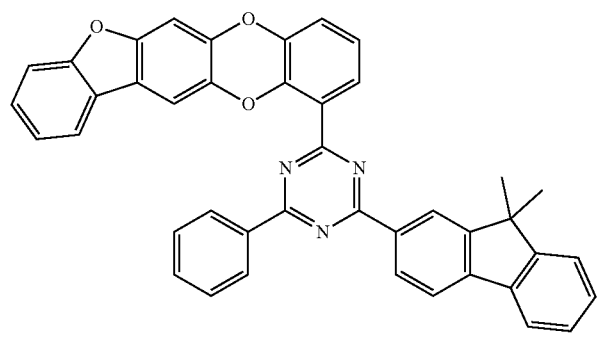
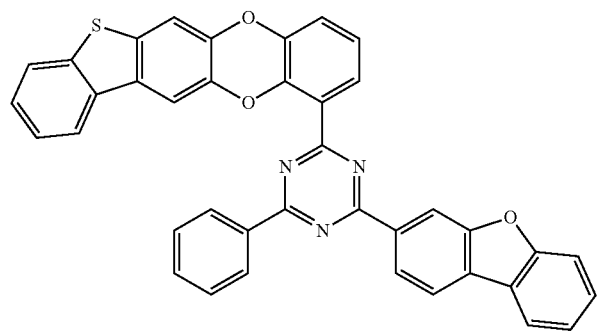
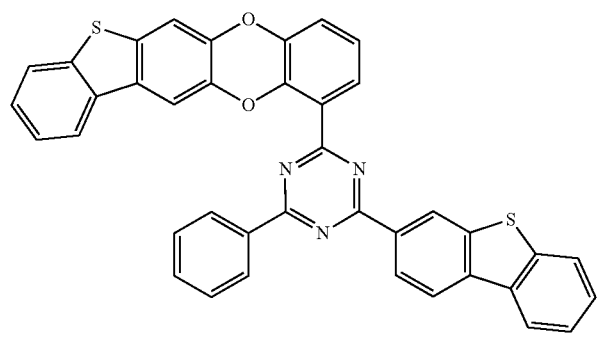

-continued
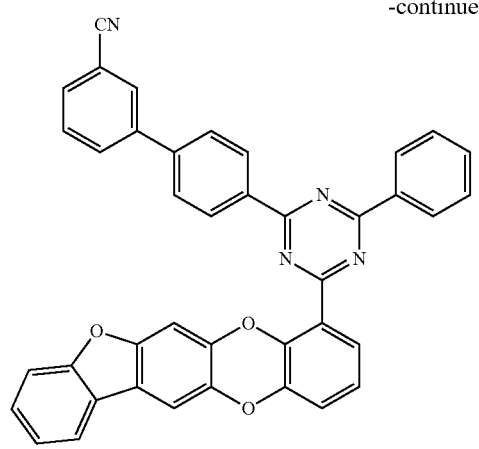
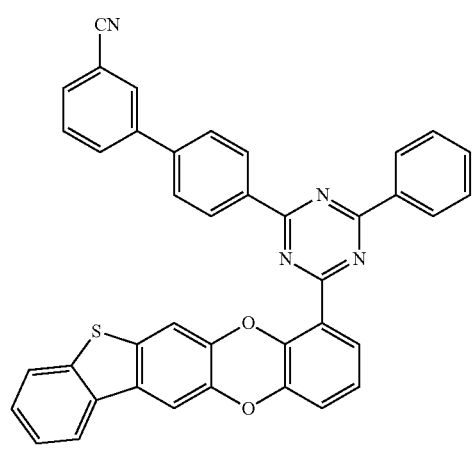
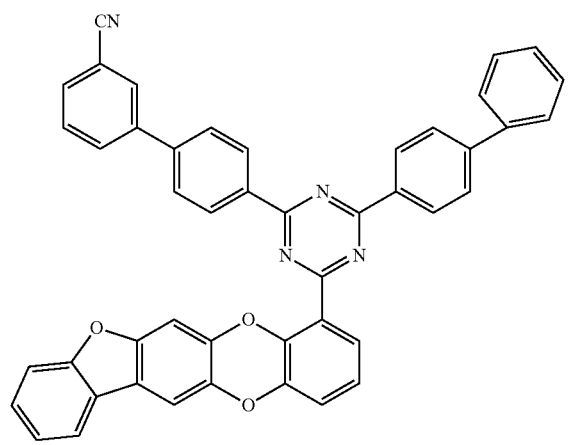

-continued
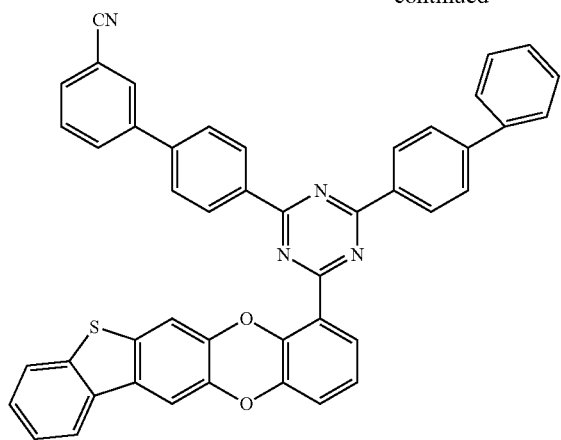
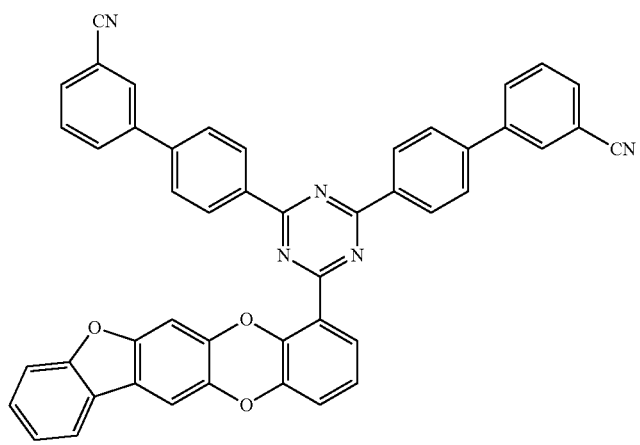
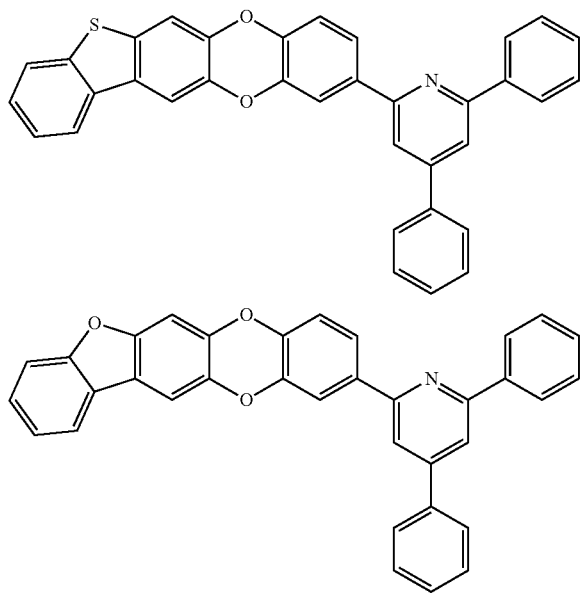

-continued
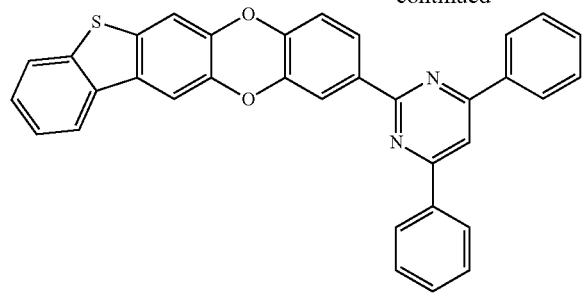
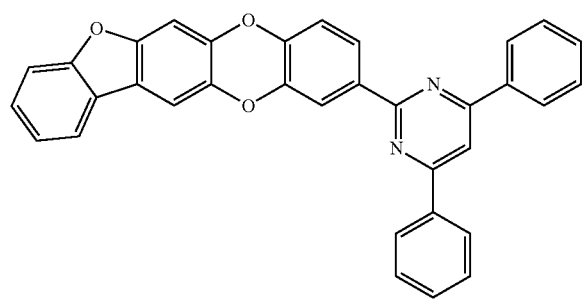
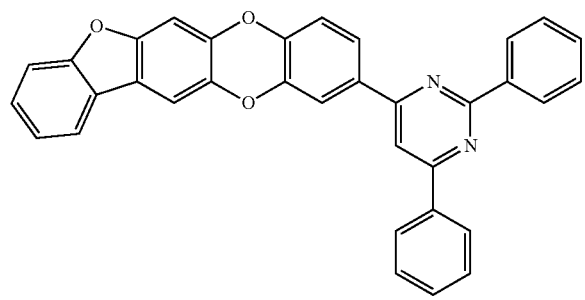
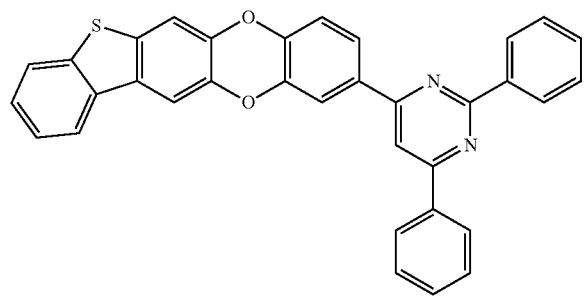
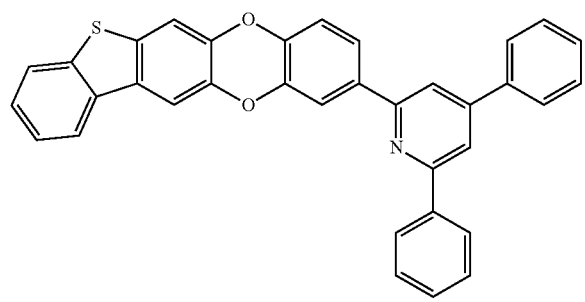

-continued
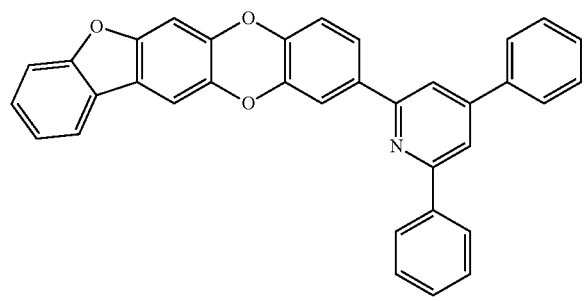
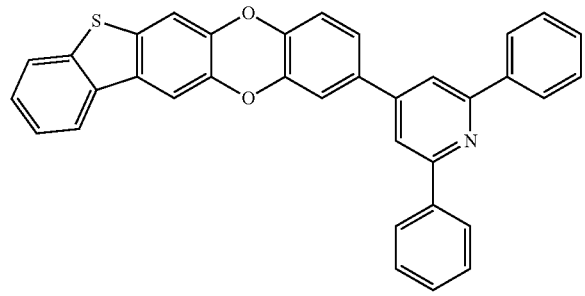
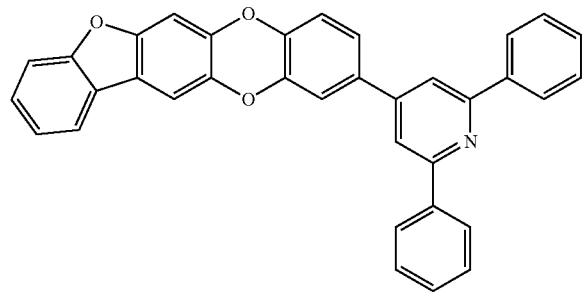
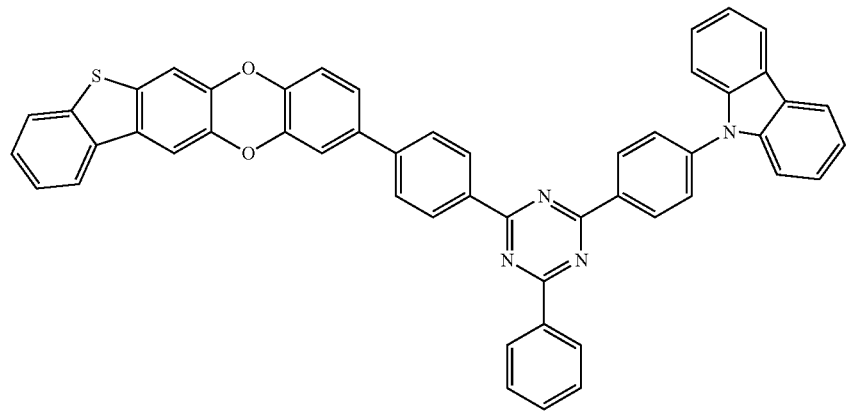
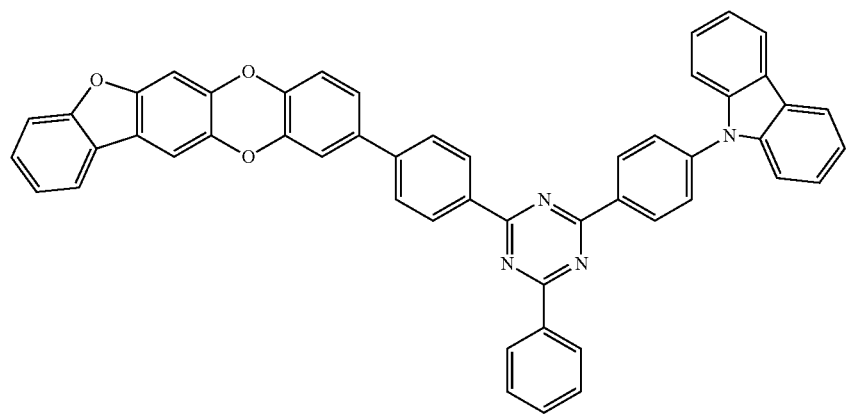

-continued
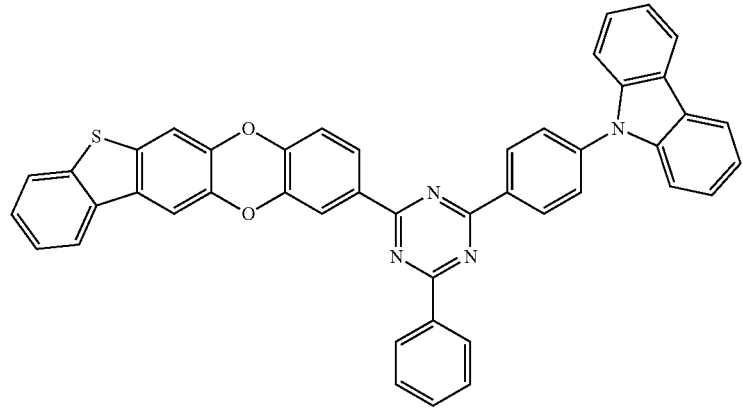
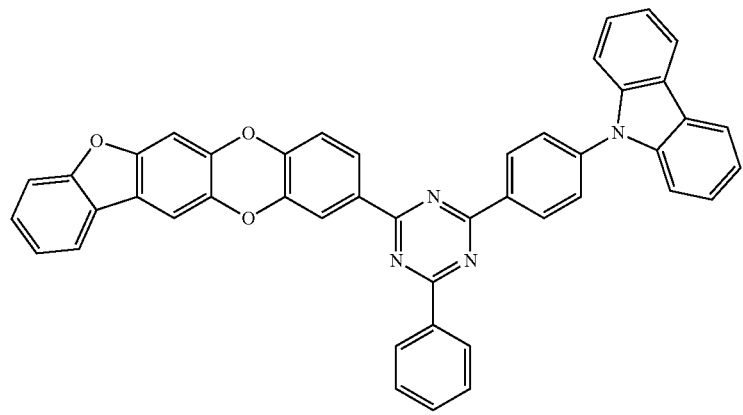
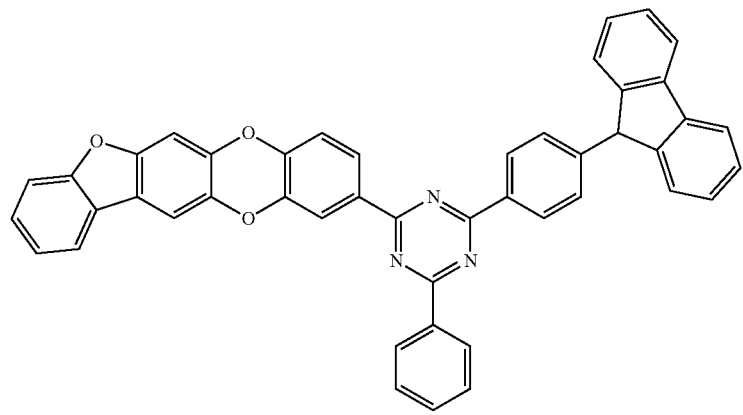
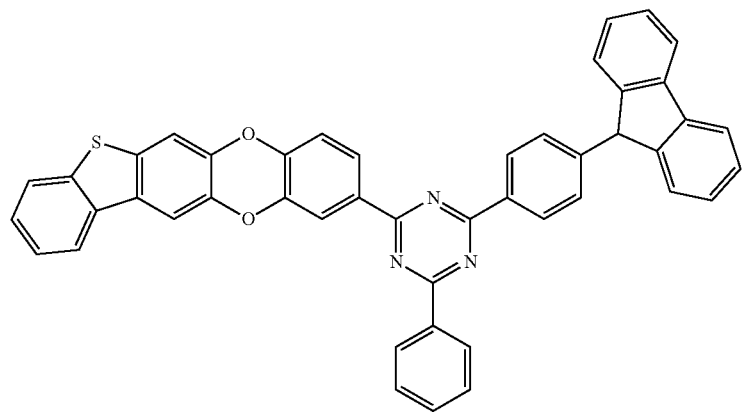

-continued
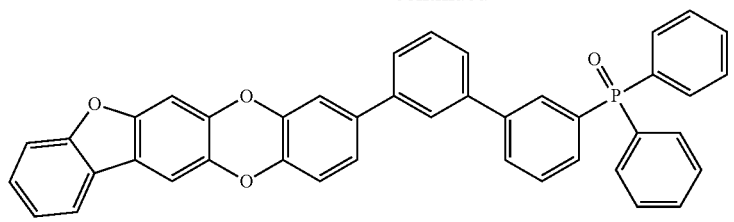
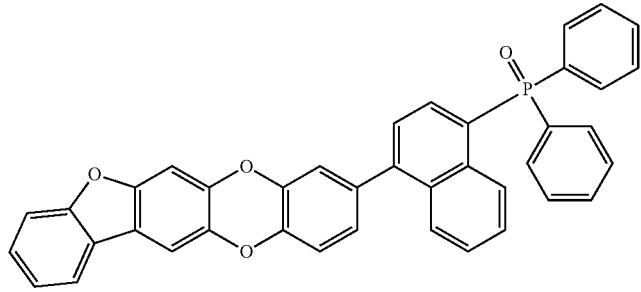
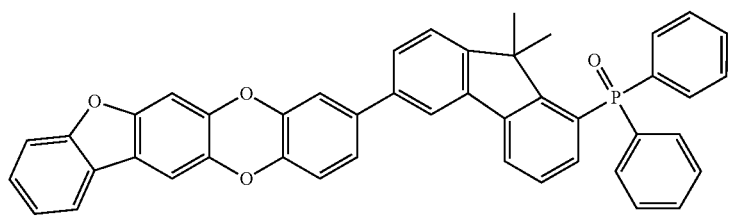
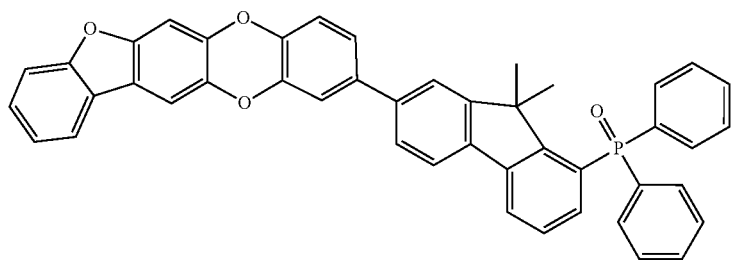
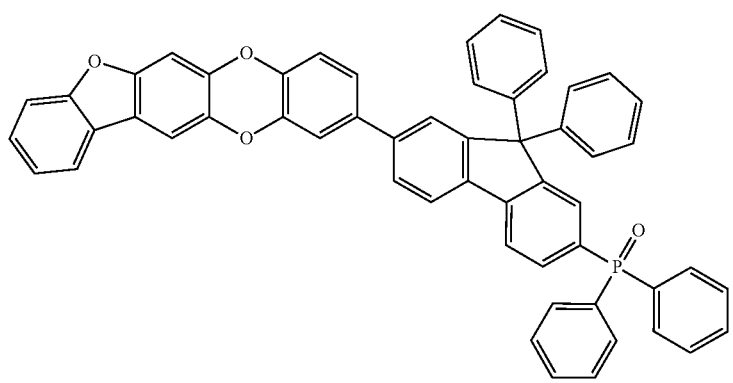
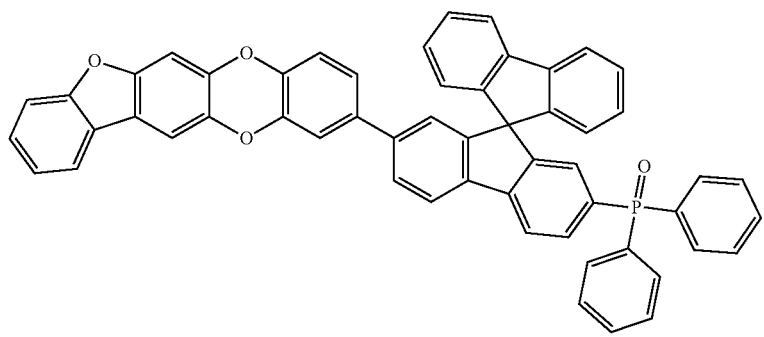

-continued
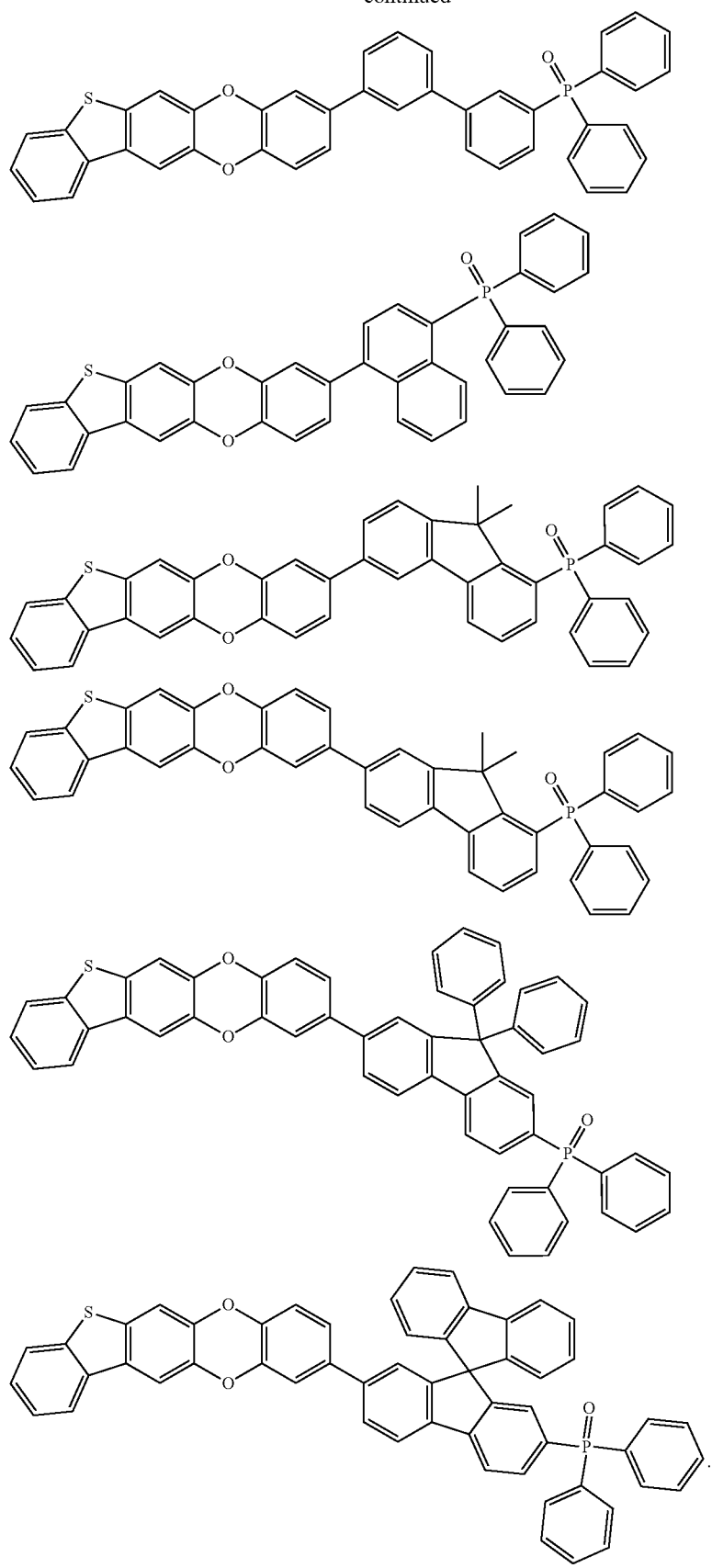

In another aspect of this application, a preparation method of the dioxin derivative mentioned above is provided, including:
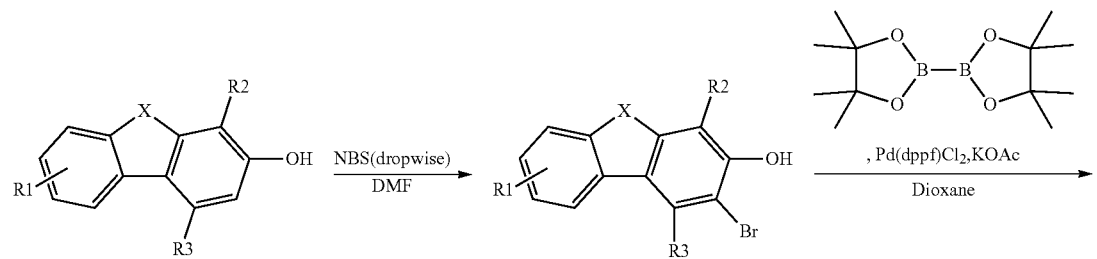
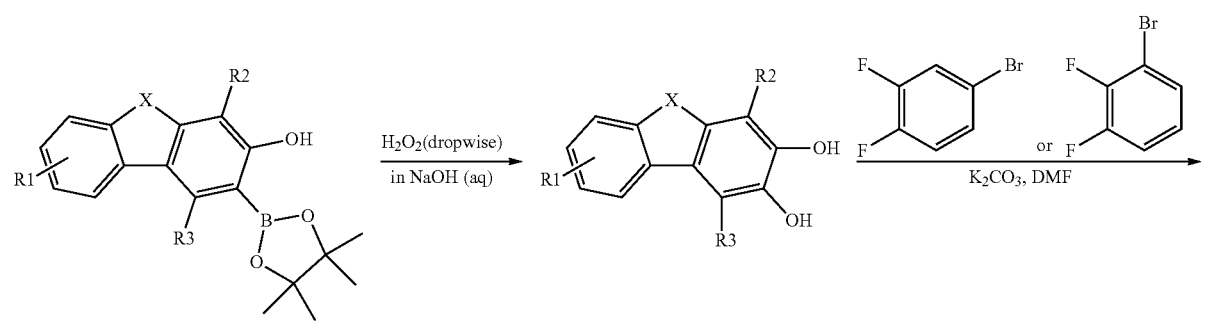
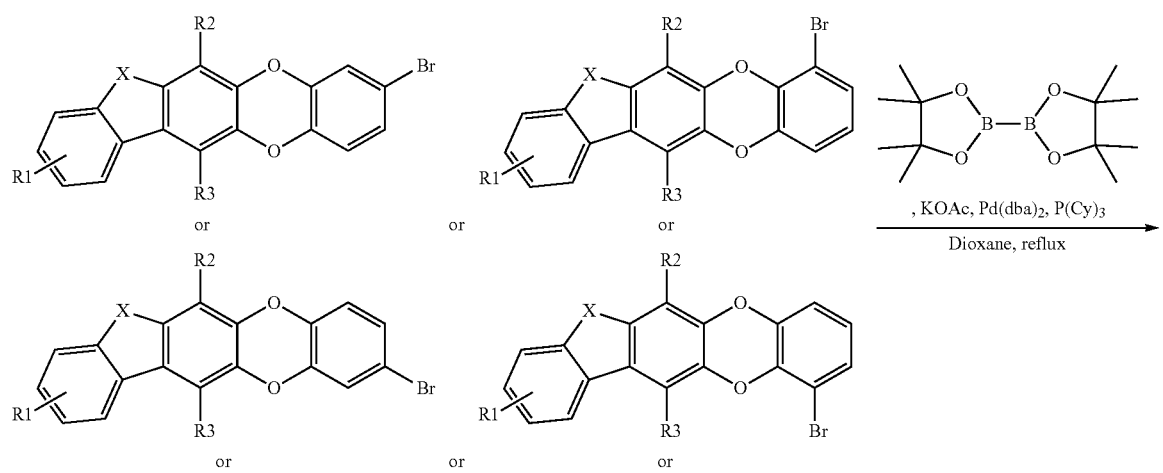

-continued

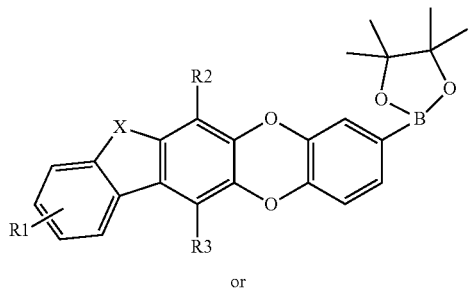

or

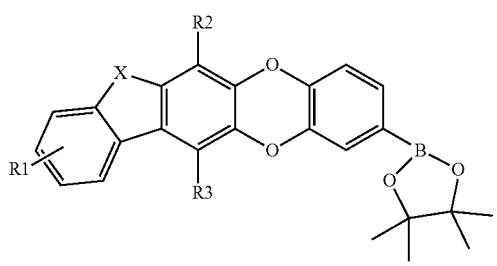

or

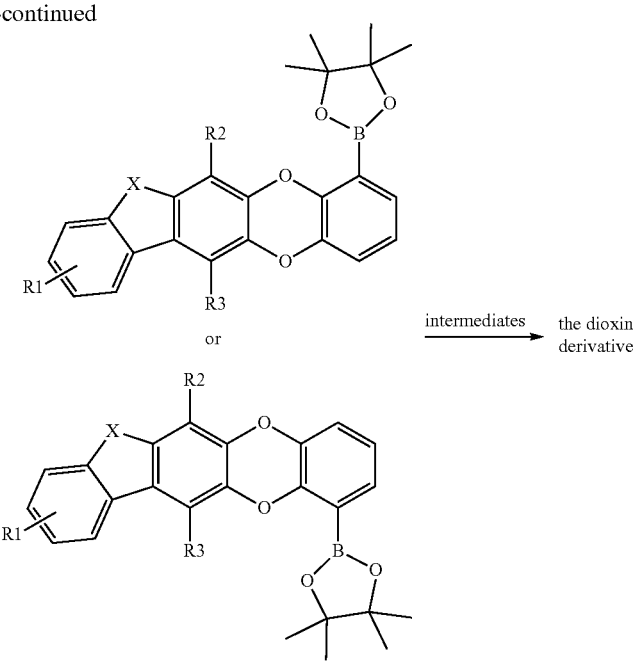

intermediates ⟶ the dioxin derivative

In another aspect of this application, an electron transport layer is provided, including the dioxin derivative mentioned above.

In another aspect of this application, an OLED device is provided, including the electron transport layer mentioned above.

In another aspect of this application, a display panel is provided, including the OLED device mentioned above.

DETAILED DESCRIPTION OF THE EMBODIMENTS

The embodiments of the present application are described in detail below. The embodiments described below are exemplary, and only used to explain this application, but should not be construed as limiting this application. Means or conditions not specified in the embodiments shall be carried out in accordance with means or conditions in literature of this field or in accordance with product specifications. Reagents or materials used here without manufacturer's indication are all conventional products that can be commercially purchased.

As one of the core materials of OLEDs, organic electron transport materials of an organic functional layer in OLEDs have an important influence on performance and stability of OLEDs. An electron transport material (ETM) should have a higher electron mobility ($\mu_e$), a higher glass transition temperature ($T_g$), a higher triplet state energy level ($E_T$), a deeper HOMO energy level and an appropriate LUMO energy level. When choosing an ETM with such characteristics as an electron transport layer, the OLED device has higher efficiency. However, many materials are complex in design and synthesis, and difficult to prepare and purify, which limits the application of electron transport materials and hole blocking materials in OLEDs.

In an aspect of this application, a dioxin derivative is provided of a formula:

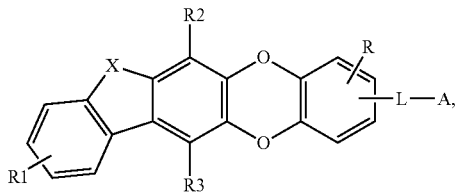

where X is O, S or NR. R, R1, R2 and R3 independently are hydrogen, deuterium, halogen, cyano, nitro, $C_1$-$C_{40}$ alkyl, $C_2$-$C_{40}$ alkenyl, $C_2$-$C_{40}$ alkynyl, $C_3$-$C_{40}$ cycloalkyl, $C_3$-$C_{40}$ heterocycloalkyl, $C_6$-$C_{60}$ aryl, $C_5$-$C_{60}$ heteroaryl, $C_1$-$C_{40}$ alkoxy, $C_6$-$C_{60}$ aryloxy, $C_3$-$C_{40}$ alkylsilyl, $C_6$-$C_{60}$ arylsilyl, $C_1$-$C_{40}$ alkylboryl, $C_6$-$C_{60}$ arylboryl, $C_6$-$C_{60}$ arylphosphonoyl, $C_6$-$C_{60}$ mono- or di-arylphosphanyl, or $C_6$-$C_{60}$ arylamino. L represents a direct bond (which means that L is a single bond connecting A), or L is a substituted or unsubstituted $C_6$-$C_{60}$ arylene, or L is a $C_2$-$C_{60}$ heteroaryl containing a first heteroatom. A has a formula of

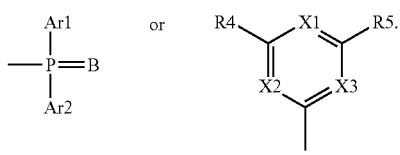

Ar1 and Ar2 independently are substituted or unsubstituted aryl, phenyl, biphenyl, or heterocyclyl containing a second heteroatom. B is O, S or Se. X1, X2 and X3 independently are C or N, and at least one of X1, X2 or X3 is N. R4 and R5 independently are $C_5$-$C_{30}$ aromatic or heteroaromatic group ring. Therefore, the dioxin derivative mentioned above has a large conjugated π-system, and the continuous conjugated T-system brings a relatively good electron mobility, especially when the dioxin derivative is fused with a benzofuran or a benzothiophene, so that the dioxin derivative in this application has a high electron mobility, is easy to disperse and transfer charges, and has a good stability, an excellent charge transport ability and a high glass transition temperature. A series of substitutions exist in structure of the dioxin derivative, which makes its molecule have a better stereo structure, so as to effectively prevent the derivative from crystallizing. This kind of molecule has a higher triplet state energy level (T1), and can effectively prevent excitons generated in the light-emitting layer from diffusing to the electron transport area when applied in an electron transport layer of an OLED device, thereby improving efficiency of the device. Thus, an electron transport layer made of the dioxin derivative can bring an OLED device a lower voltage and a good luminous efficiency.

Optionally, when X1, X2 and X3 are all N,

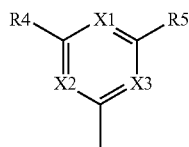

includes a triazine group which is a potent electron-withdrawing group, so that the dioxin derivative in this application has a higher electron mobility and a deeper HOMO energy level, and can block holes well, which endows an OLED device with a relatively low voltage and a good luminous efficiency.

According to an embodiment of this application, the first heteroatom is at least one of N, O, S or Si, and the second heteroatom is at least one of N, O or S. Thus, the dioxin derivative is easy to prepare, and can be effectively endowed with the good properties mentioned above.

According to an embodiment of this application, at least one of R4 or R5 may be substituted by R3. Thus, this application provides multiple types of the dioxin derivative, which gives more options.

According to an embodiment of this application, at least one of R4 or R5 contains a third heteroatom, and the third heteroatom is at least one of N, S or B. Thus, the dioxin derivative is easy to prepare, and can be effectively endowed with the good properties mentioned above.

In some embodiments, a first group and a second group bonding to the same third heteroatom are bonded with a single bond, that is, the first group and the second group respectively connected to the third heteroatom are directly connected with each other through a chemical bond, so as to form a heterocycle composed of the third heteroatom, the first group and the second group. In other embodiments, the first group and the second group are bridged with a third group, where the third group is selected from B(R3), C(R3)$_2$, Si(R3)$_2$, C=O, C=N(R3), C=C(R3)$_2$, O, S, S=O, SO$_2$, N(R3), P(R3) and P(=O)R3, that is, the first group and the second group are respectively connected to the B, C, O, S, Si, N or P in the third group through a chemical bond, so as to form a heterocycle composed of the third heteroatom, the first group, the second group and the B, C, O, S, Si, N or P of the third group. Thus, the specific types of the dioxin derivative are further increased.

It should be understood that the above mentioned B, C, O, S, Si, N or P in the third group respectively refer to B in B(R3), C in C(R3)$_2$, C=O, C=C(R3)$_2$ or C=N(R3), O in O, S in S=O or SO$_2$ or S, Si in Si(R3)$_2$, N in N(R3), P in P(R3) or P(=O)R3.

According to an embodiment of this application, the first group and the second group independently are a phenyl, an aryl or an alkyl. Thus, the dioxin derivative is easy to prepare, and can be effectively endowed with the good properties mentioned above, and specific types of the dioxin derivative are further increased.

According to some embodiments of this application, the dioxin derivative may be one of the followings:

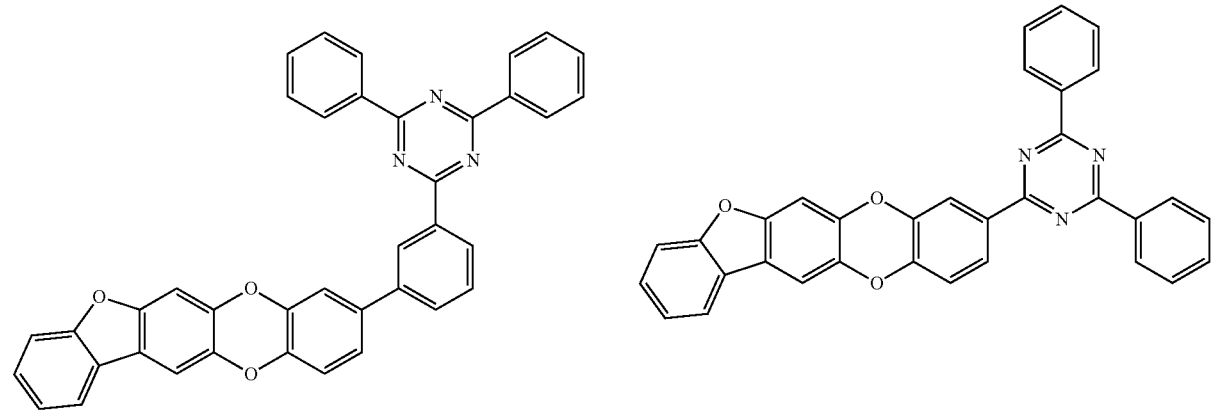

-continued
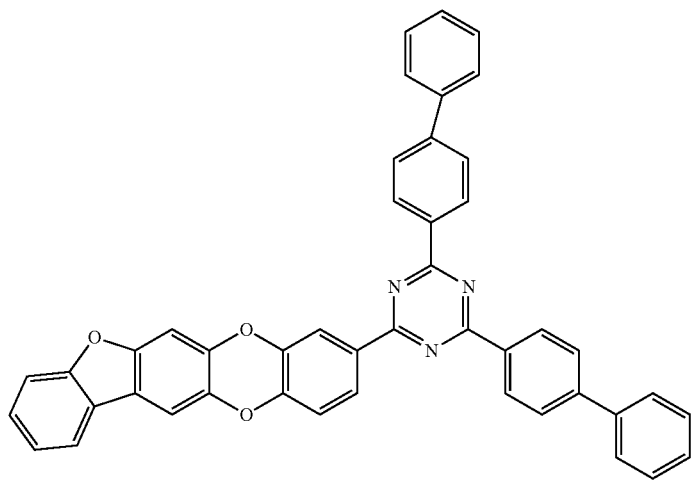
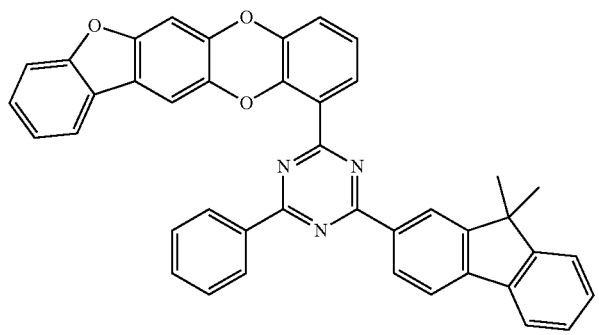
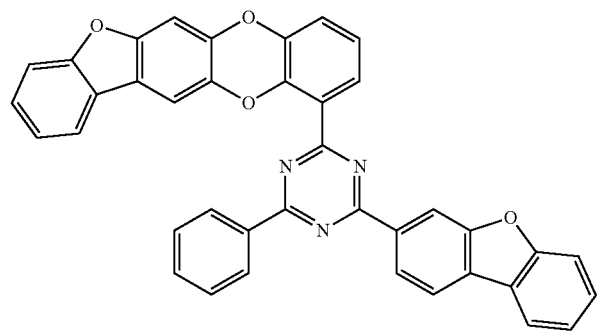
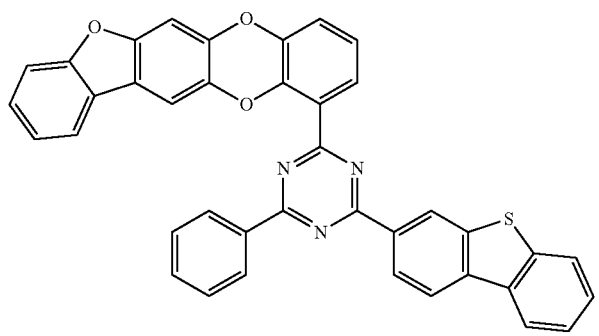
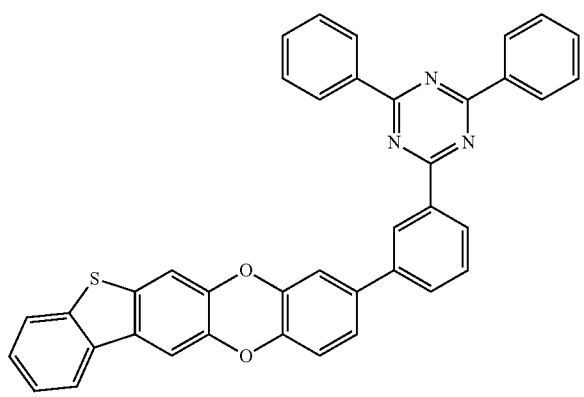
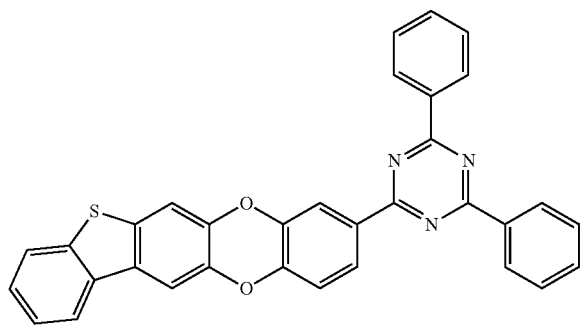

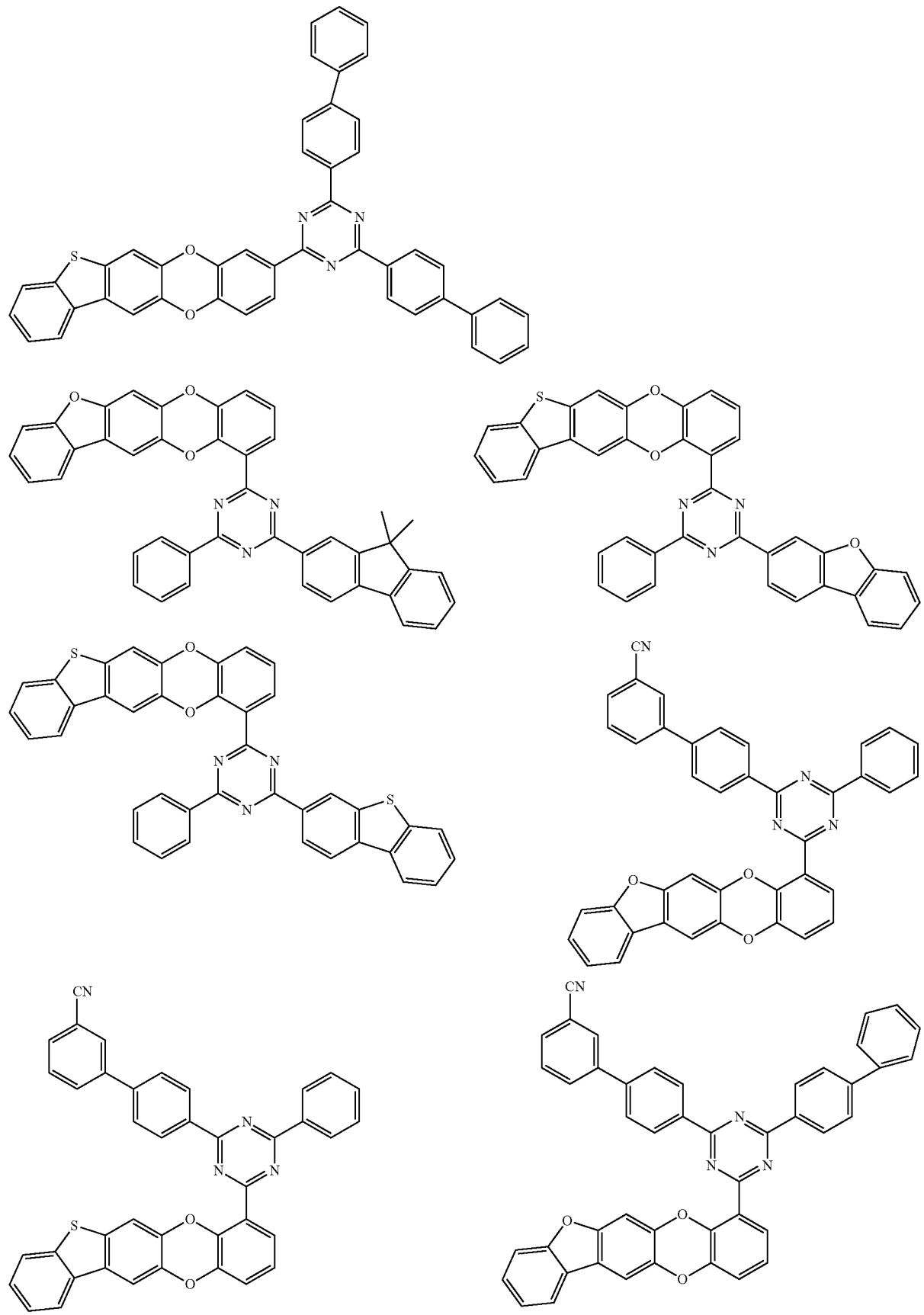

-continued
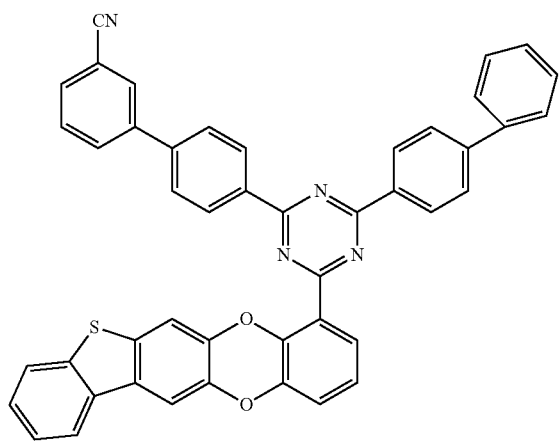
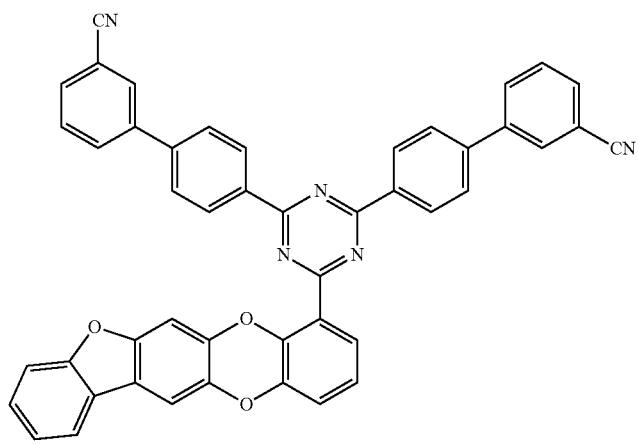
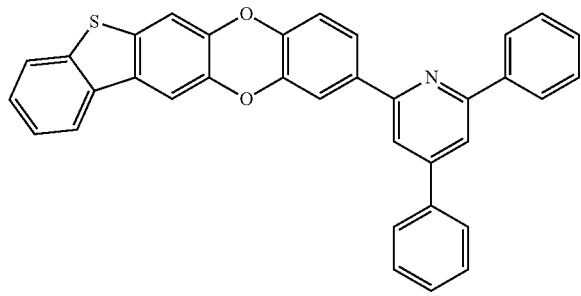
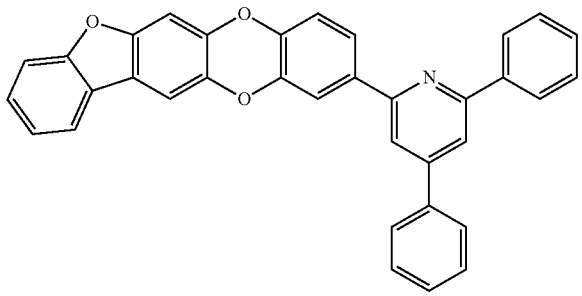
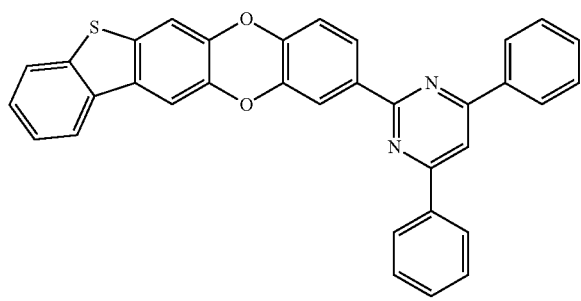
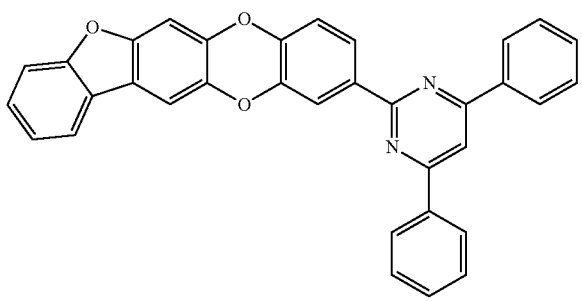

-continued
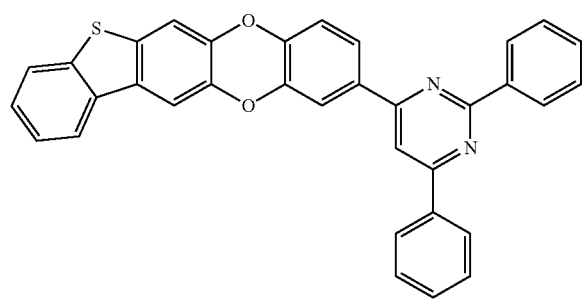
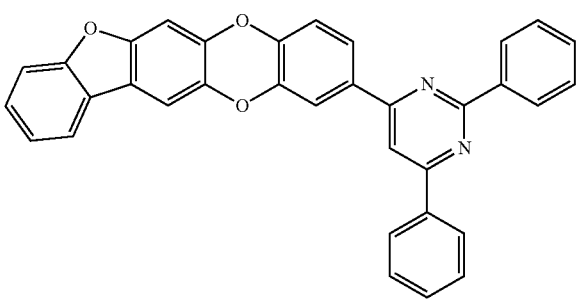
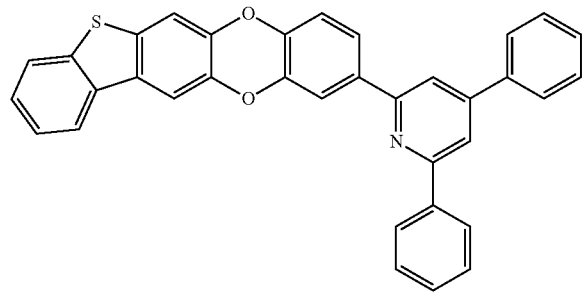
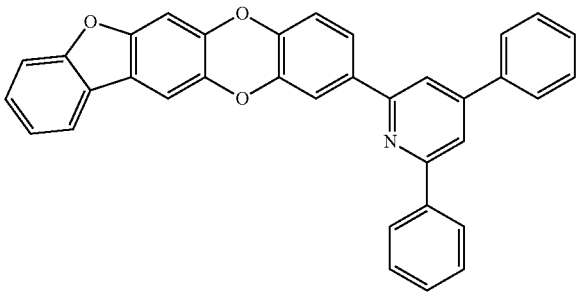
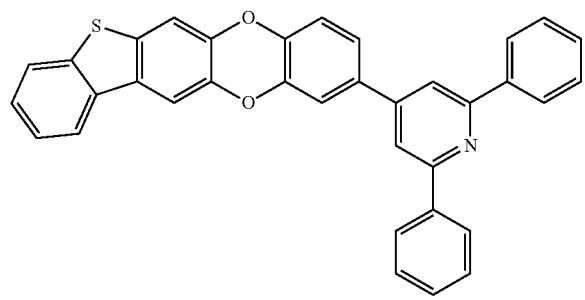
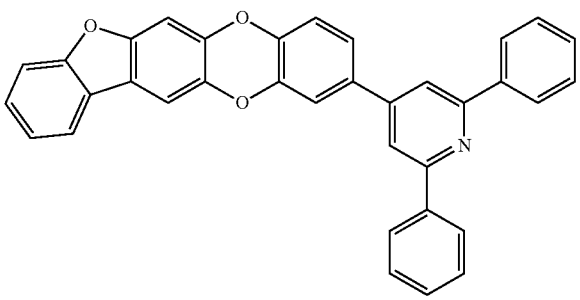
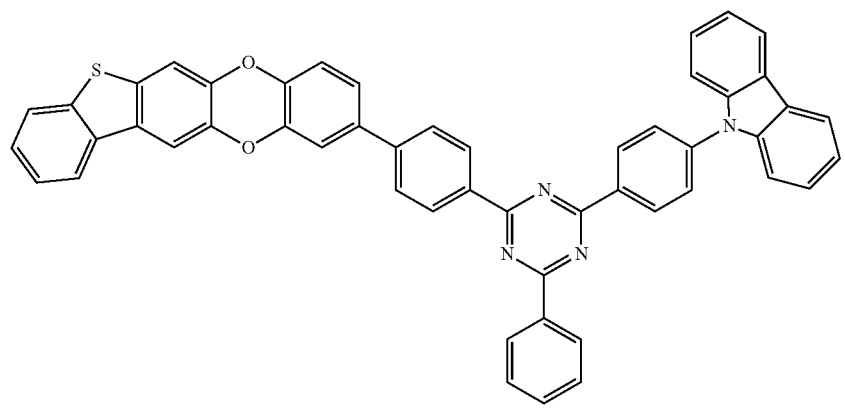
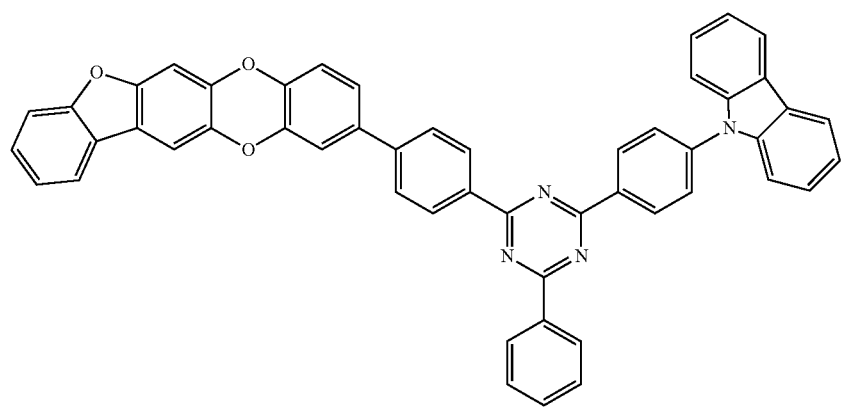

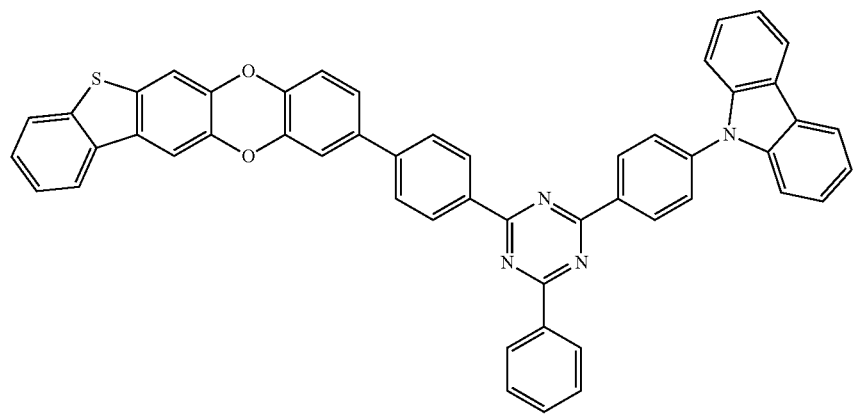
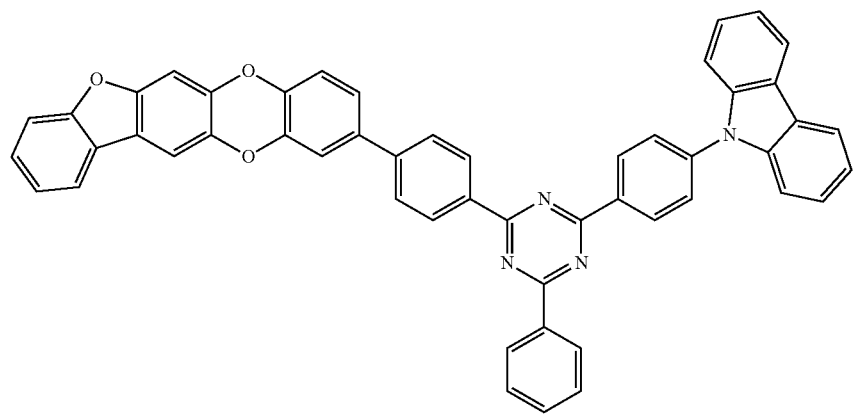
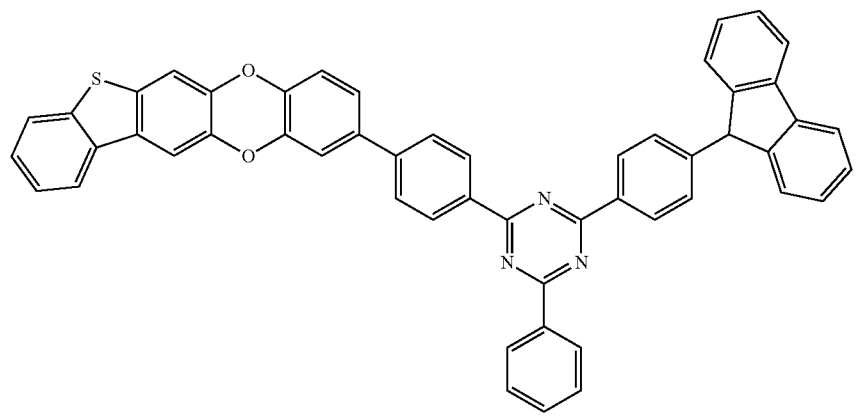
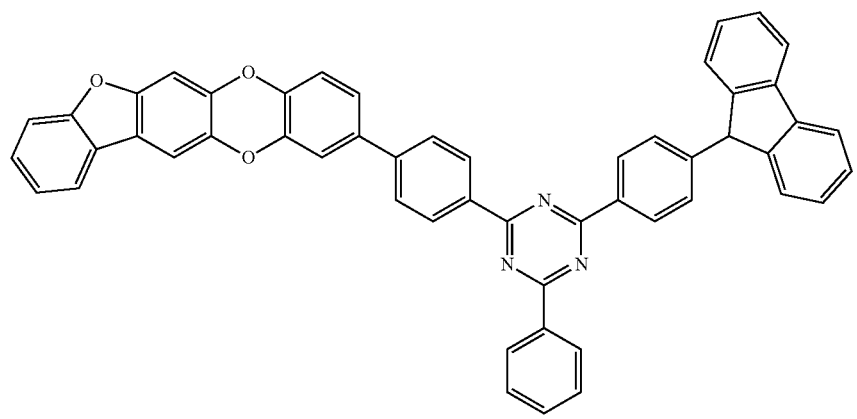

-continued
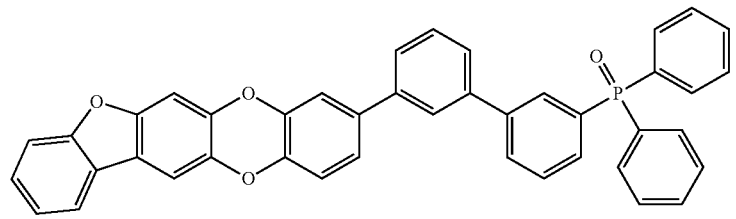
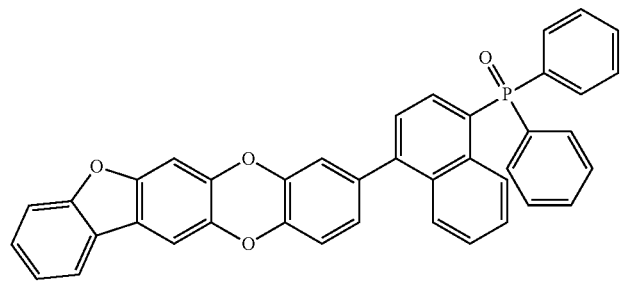
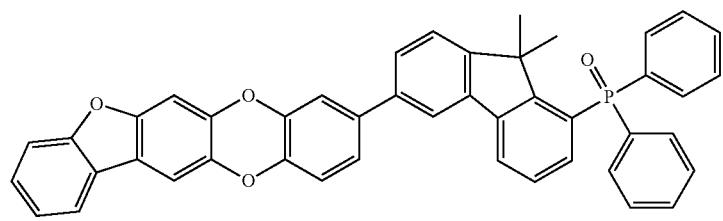
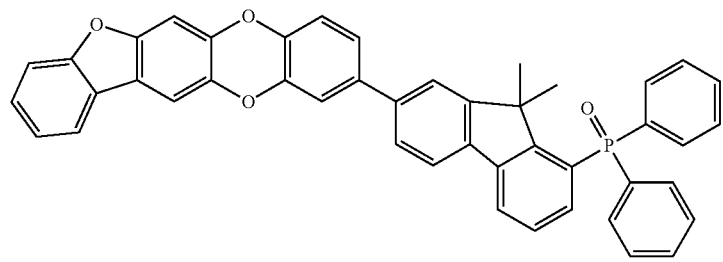
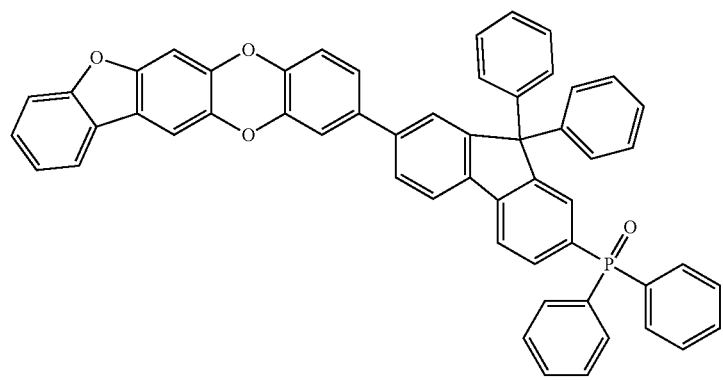
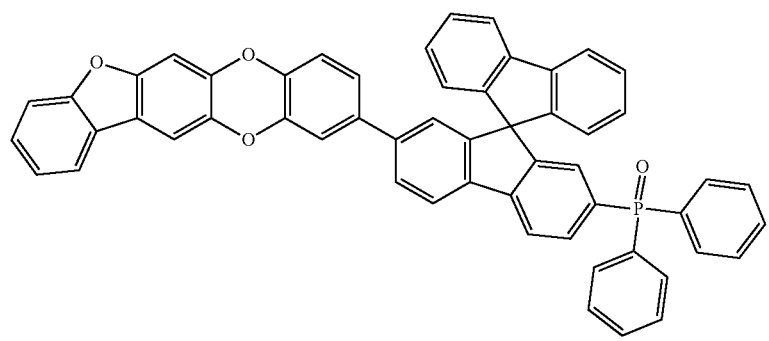

-continued
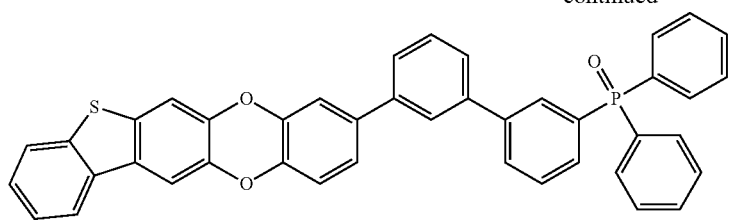
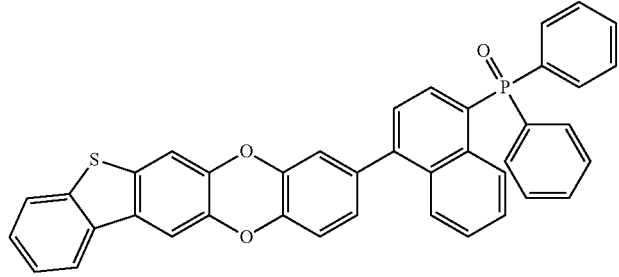
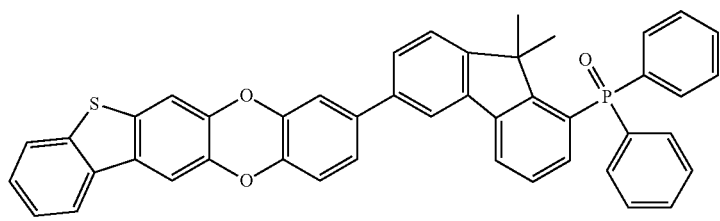
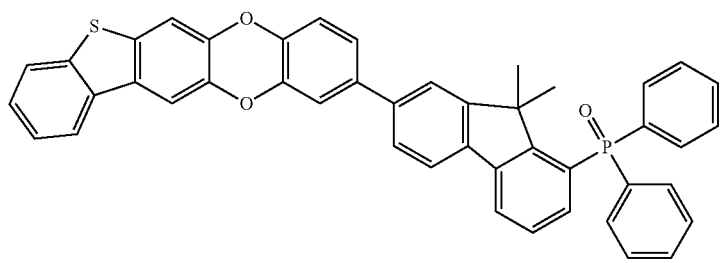
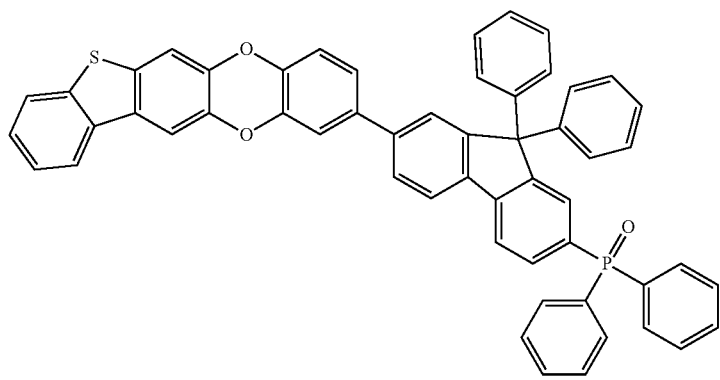
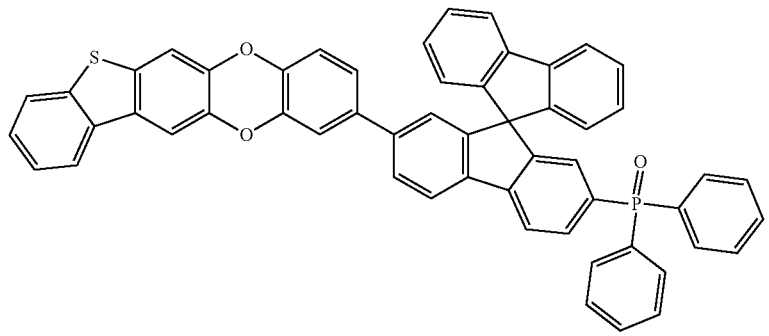

According to the embodiments of this application, the specific dioxin derivatives listed above are not only easy to prepare, but also have a good electron transport ability, a higher glass transition temperature, a higher triplet state energy level, and a relatively deep HOMO and LUMO energy level, a good stability and a high optical gap.

It should be understood that specific types of the dioxin derivative in this application are not limited to the above-listed ones. Compounds satisfying the formula of the dioxin derivative mentioned above are all within the protection scope of this application.

In another aspect of this application, a preparation method of the dioxin derivative mentioned above is provided. According to an embodiment of this application, the preparation method includes:

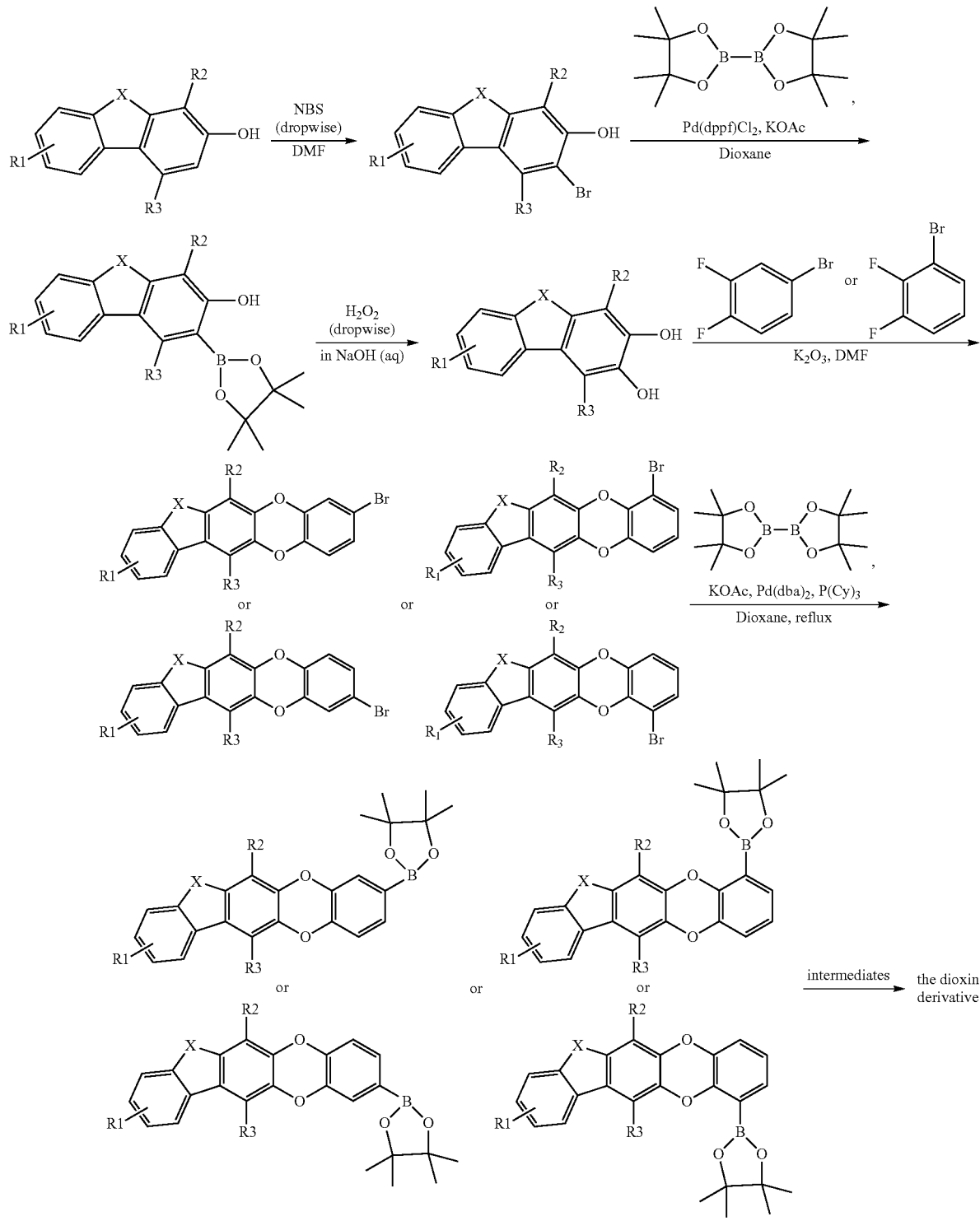

Therefore, the preparation method has good practicability, relatively mild reaction conditions, is convenient for industrial production, and has good yield and purity.

The specific type of the intermediates is not limited. Those skilled in the art may choose the intermediates with flexibility according to the above mentioned formula

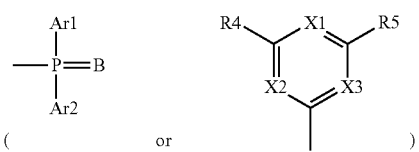

of A and the specific structure of the dioxin derivative to be prepared, and no restriction is proposed here.

According to an embodiment of this application, process of preparing the dioxin derivative is:

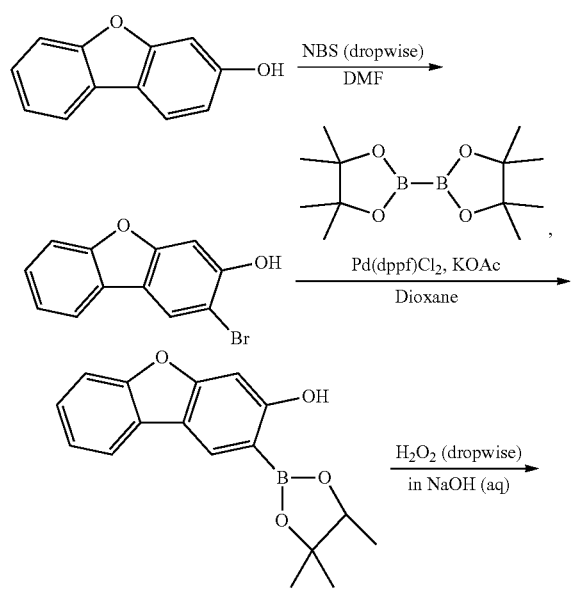

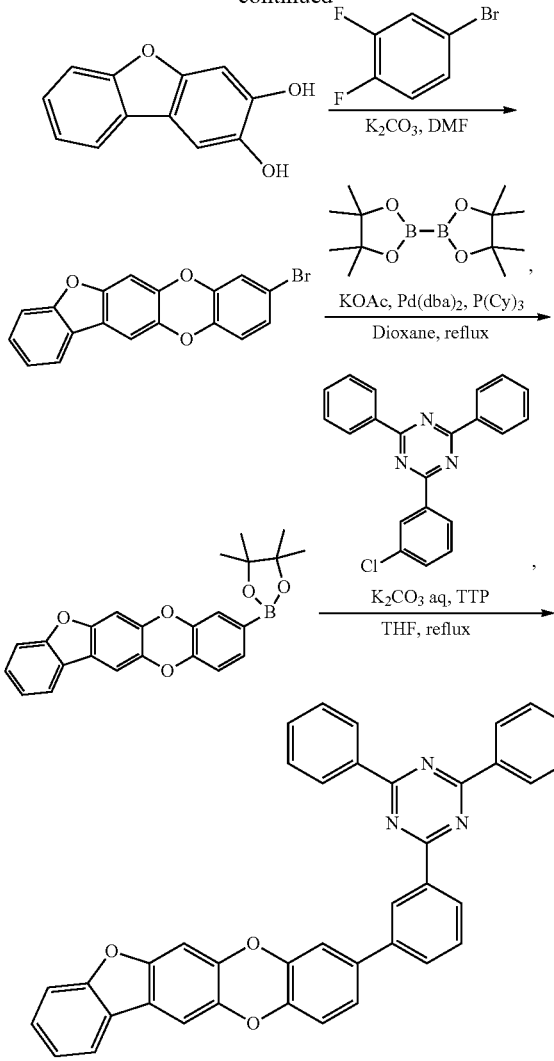

According to another embodiment of this application, process of preparing the dioxin derivative is:

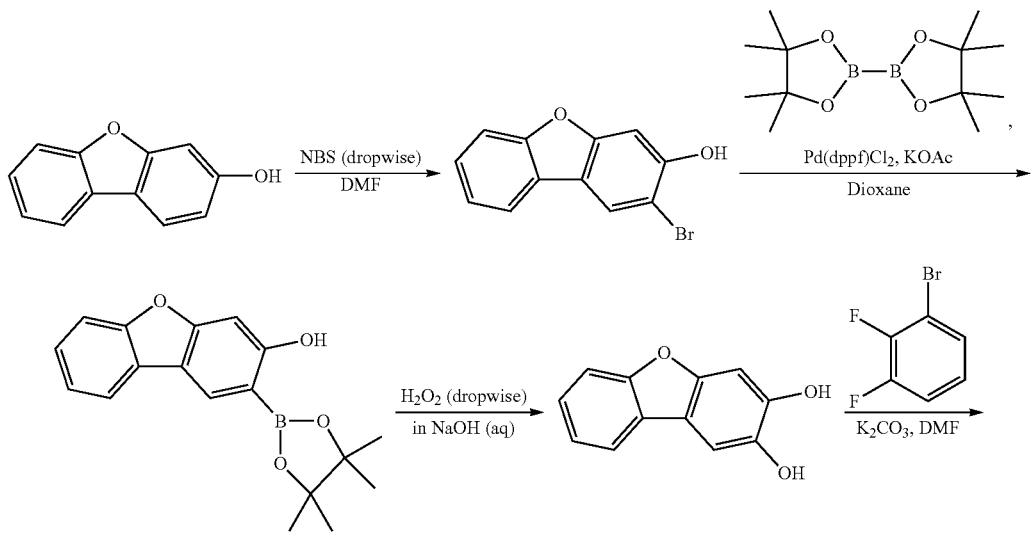

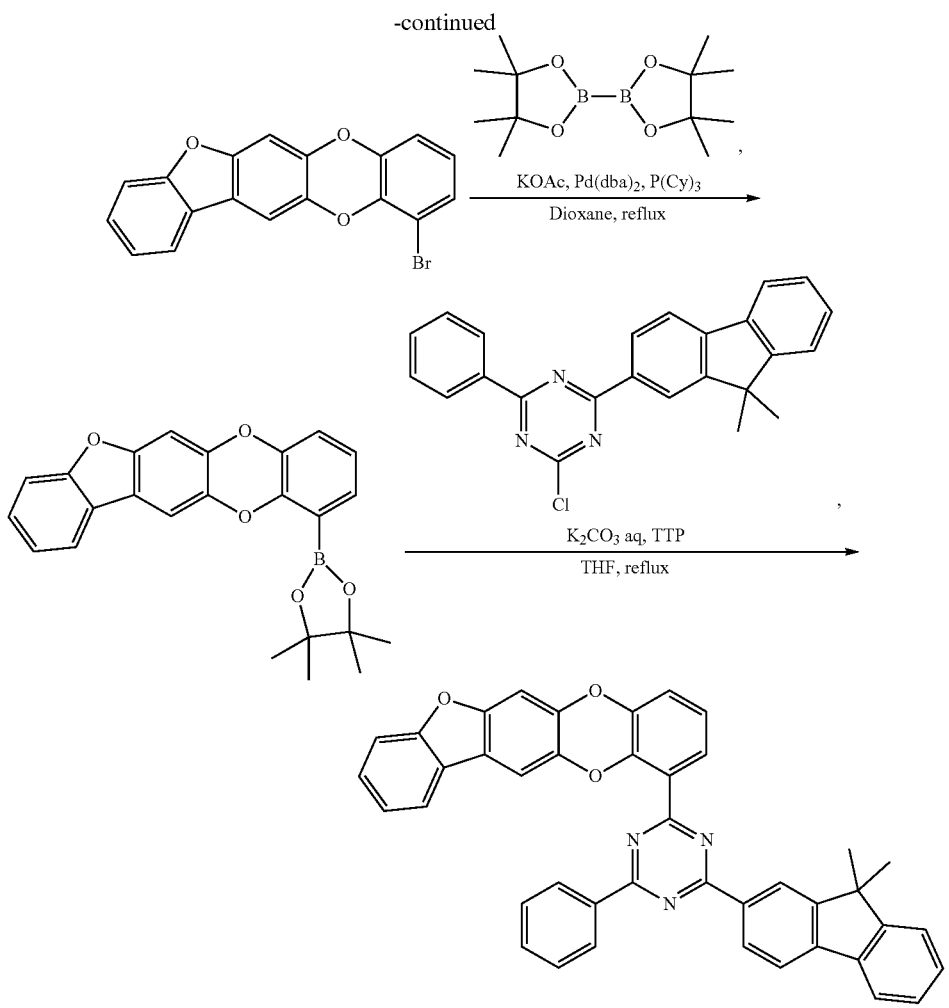
According to still another embodiment of this application, process of preparing
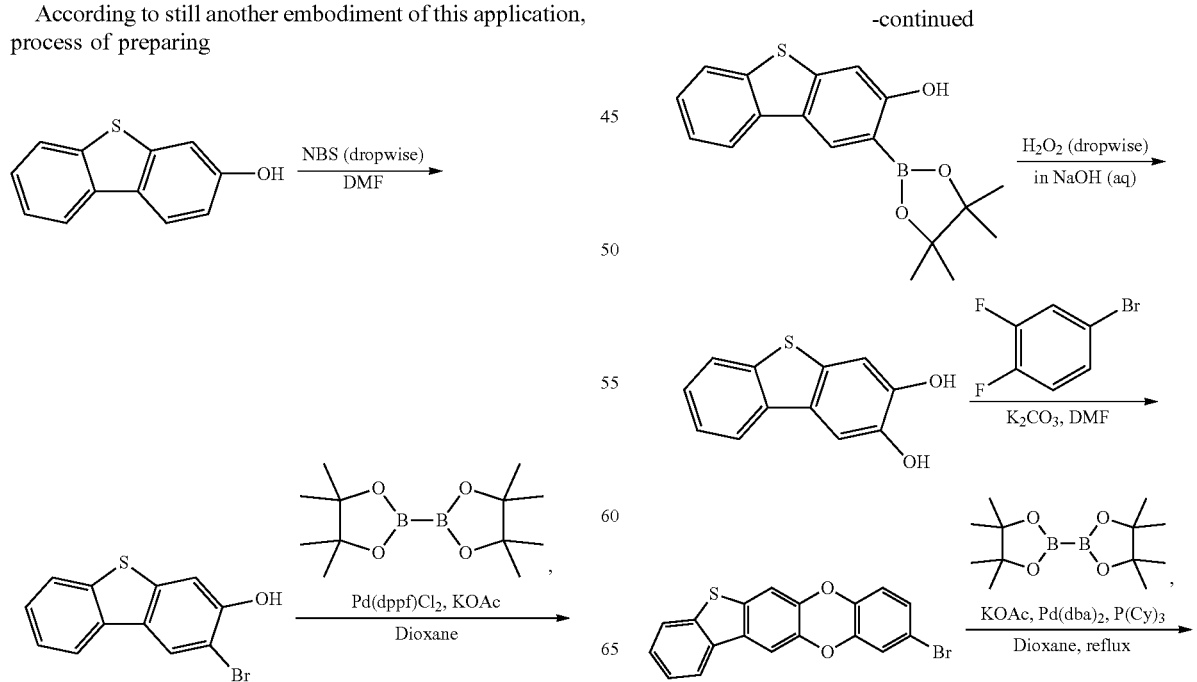

-continued

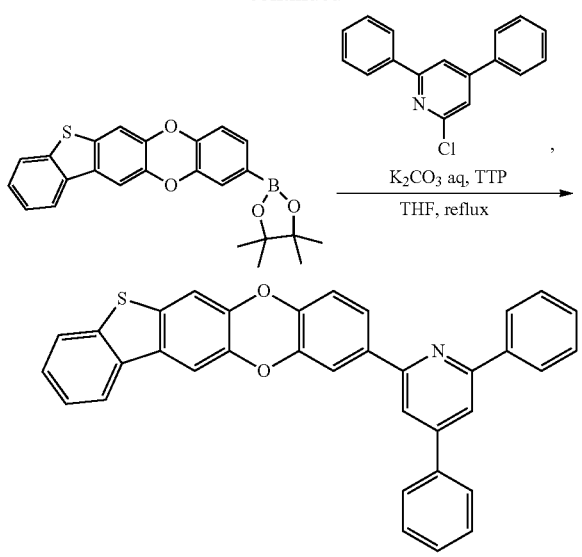

According to yet another embodiment of this application, process of preparing the dioxin derivative is:

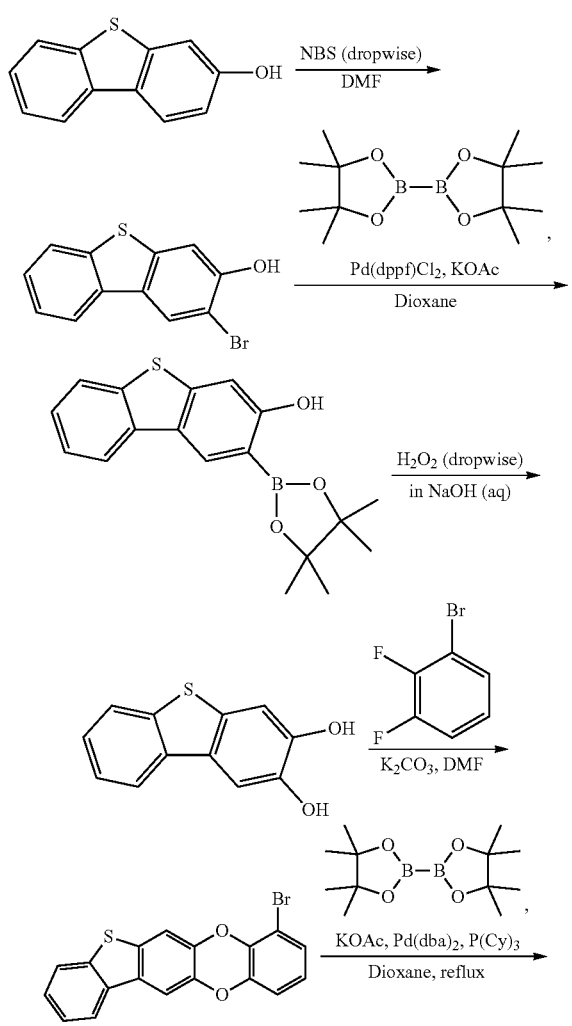

-continued

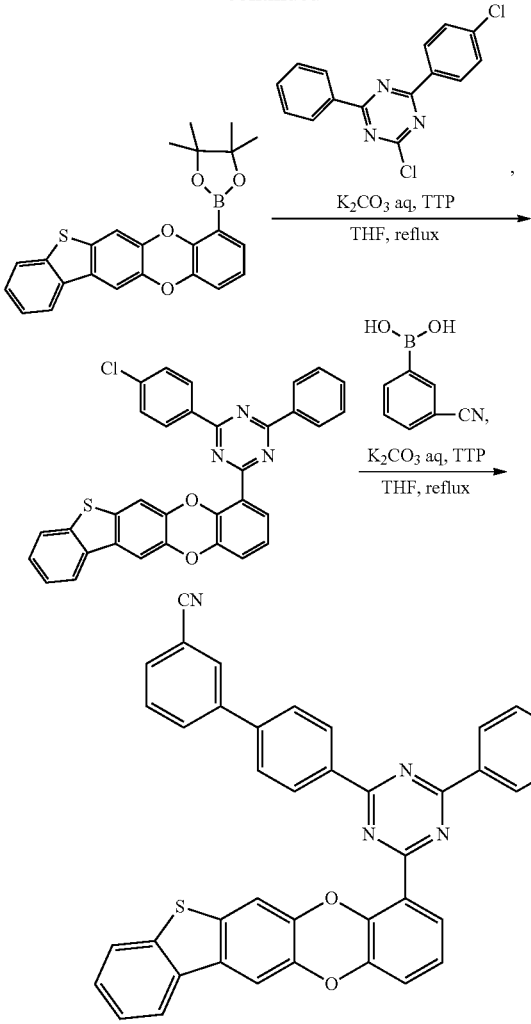

In another aspect of this application, an electron transport layer is provided. According to an embodiment of this application, the electron transport layer includes the dioxin derivative mentioned above. Thus, the electron transport layer in this application has a high electron mobility, enables charges to disperse and migrate easily, and has a good film stability, a good electrochemical stability, a good thermal stability, a good charge transport ability and a high glass transition temperature. The dioxin derivative in the electron transport layer has less possibility to crystallize. The electron transport layer can effectively prevent excitons generated in a light-emitting layer from diffusing to an electron transport area, thereby improving efficiency of an OLED device, and further bringing about a lower voltage and a good luminous efficiency.

In another aspect of this application, an OLED device is provided. According to an embodiment of this application, the OLED device includes the electron transport layer mentioned above. Thus, the OLED device has a lower voltage, a good luminous efficiency and a good stability. Those skilled in the art shall understand that the OLED device has all features and advantages of the electron transport layer mentioned above, which are not repeated here.

According to an embodiment of this application, the OLED device includes an anode, a hole injection layer (HIL), a hole transport layer (HTL), an emission layer (EML), an electron transport layer (ETL), an electron injection layer (EIL) and a cathode, which are provided in sequence as stacked layers. The anode includes ITO; and the HIL includes at least one of $MoO_3$, F4-TCNQ or HAT-CN. The HTL includes at least one of NPB, m-MTDATA or TPD; and the EML is a three-layer stack composed of an electron block layer (EBL), a light-emitting material layer and a hole block layer (HBL), where the EBL includes at least one of mCBP or Tris-PCz, the light-emitting material layer includes a Host and a Dopant, the Host is ADN, the Dopant is DPVBi, the HBL includes at least one of BCP or Bphen. The ETL includes the dioxin derivative mentioned above; the EIL includes at least one of LiY, Yb or Liq; and the cathode includes at least one of silver, magnesium or aluminum.

In another aspect of this application, a display panel is provided. According to an embodiment of this application, the display panel includes the OLED device mentioned above. Thus, display quality of the display panel is relatively good. Those skilled in the art shall understand that the display panel has all features and advantages of the OLED device mentioned above, which are not repeated here.

According to an embodiment of this application, a specific type of a display apparatus that the display panel is used for is not limited, and may be flexibly decided by those skilled in the art according to actual needs. In some embodiments, the display panel may be used in a display apparatus with display functions, such as a mobile phone, a laptop, a tablet computer, an electronic paper or a gaming console.

Those skilled in the art shall understand that besides the OLED device mentioned above, the display panel further includes essential structures or elements in an ordinary display panel, such as a thin film transistor (TFT) back panel, a color-filter substrate, a sealant and so on.

EMBODIMENTS

Embodiment 1

An OLED device includes an anode, a hole injection layer (HIL), a hole transport layer (HTL), an emission layer (EML), an electron transport layer (ETL), an electron injection layer (EIL) and a cathode, which are provided in sequence as stacked layers. Among them, the anode includes ITO; the HIL includes HAT-CN and has a thickness of 20 nm; the HTL includes NPB and has a thickness of 80 nm; the EML layer is a three-layer stack composed of an electron block layer (EBL), a light-emitting material layer and a hole block layer (HBL), where the EBL includes mCBP and has a thickness of 10 nm, the light-emitting material layer includes ADN and DPVBi and has a thickness of 30 nm, and the DPVBi accounts for 5% of the light-emitting material layer in terms of mass, the HBL includes BCP and has a thickness of 10 nm; the ETL includes dioxin derivative 1 (see Table 1 for a specific structure, a HOMO distribution and a LUMO distribution); the EIL includes LiF and has a thickness of 1 nm; and the cathode includes aluminum and has a thickness of 120 nm.

Embodiment 2

Difference from the Embodiment 1 is that the ETL includes dioxin derivative 2 (see Table 1 for a specific structure, a HOMO distribution and a LUMO distribution), and has a thickness of 30 nm.

Embodiment 3

Difference from the Embodiment 1 is that the ETL includes dioxin derivative 3 (see Table 1 for a specific structure, a HOMO distribution and a LUMO distribution), and has a thickness of 30 nm.

Embodiment 4

Difference from the Embodiment 1 is that the ETL includes dioxin derivative 4 (see Table 1 for a specific structure, a HOMO distribution and a LUMO distribution), and has a thickness of 30 nm.

Comparative Example 1

Difference from the Embodiment 1 is that the ETL includes $Alq_3$, and has a thickness of 30 nm.

TABLE 1

Figure 1B:
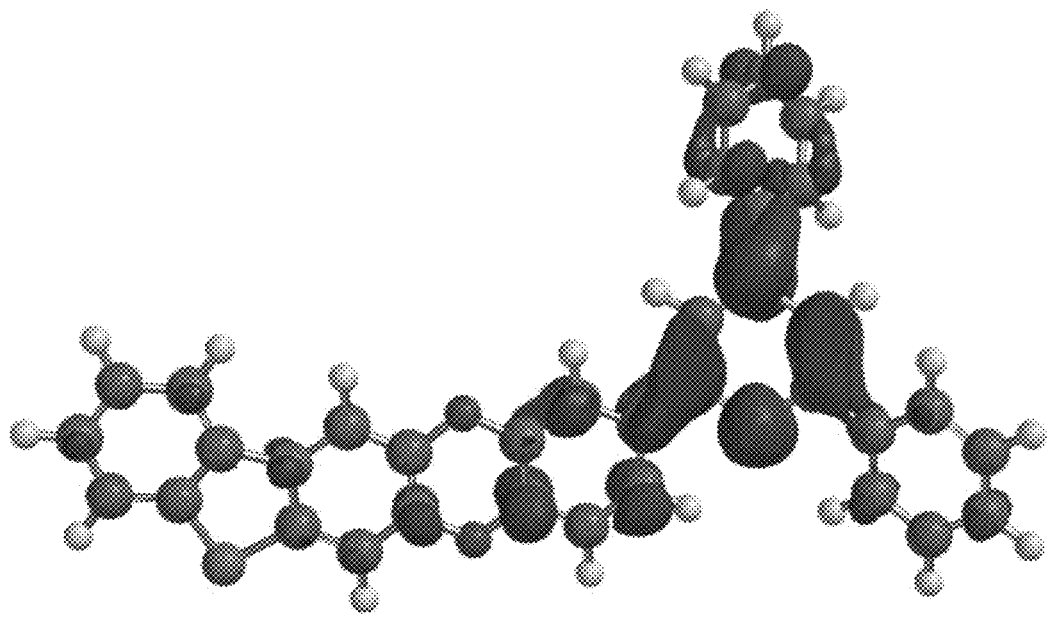

| Compound | Structure | HOMO distribution | LUMO distribution |
|---|---|---|---|
| dioxin derivative 1 | 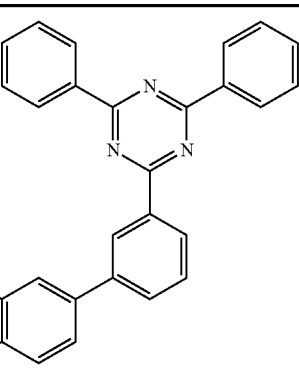 | FIG. 1A | FIG. 1B |

Figure 2A:
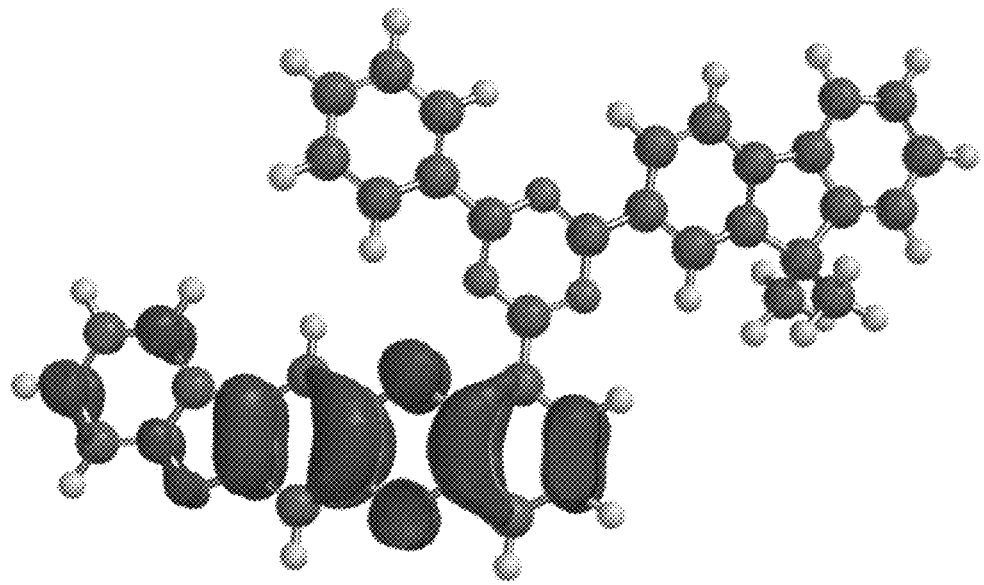
Figure 2B:
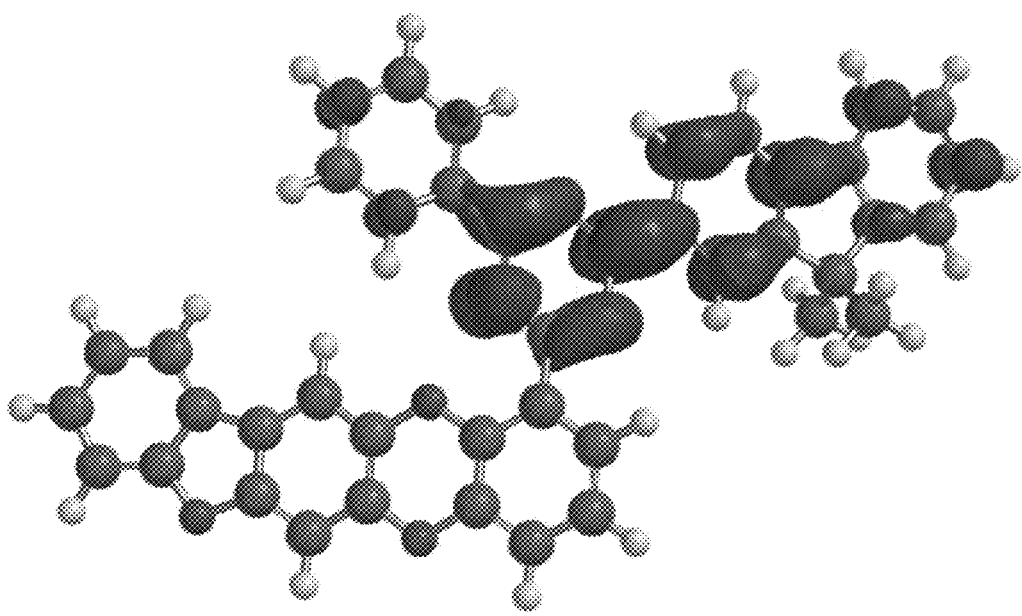
Figure 3A:
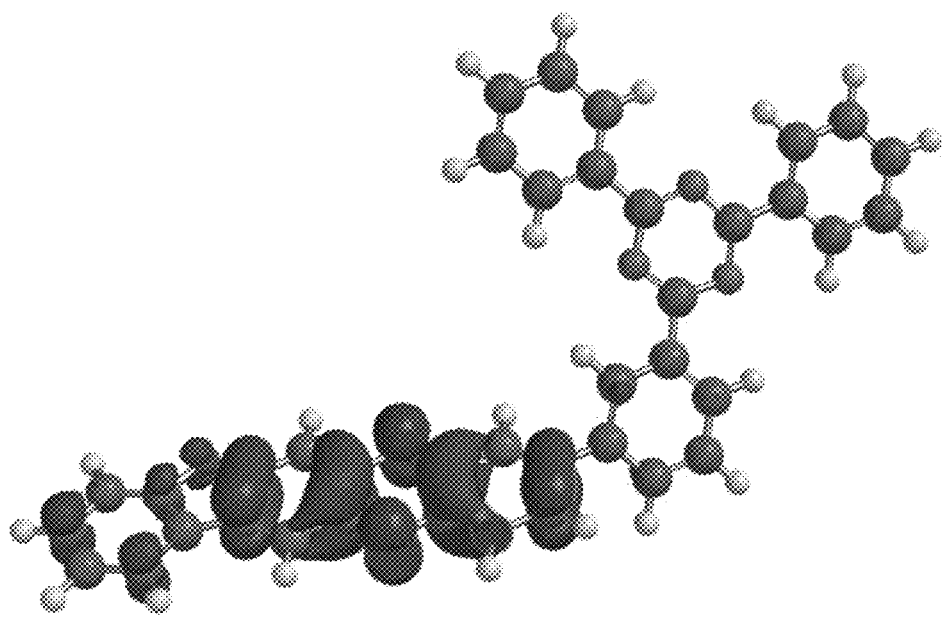
Figure 3B:
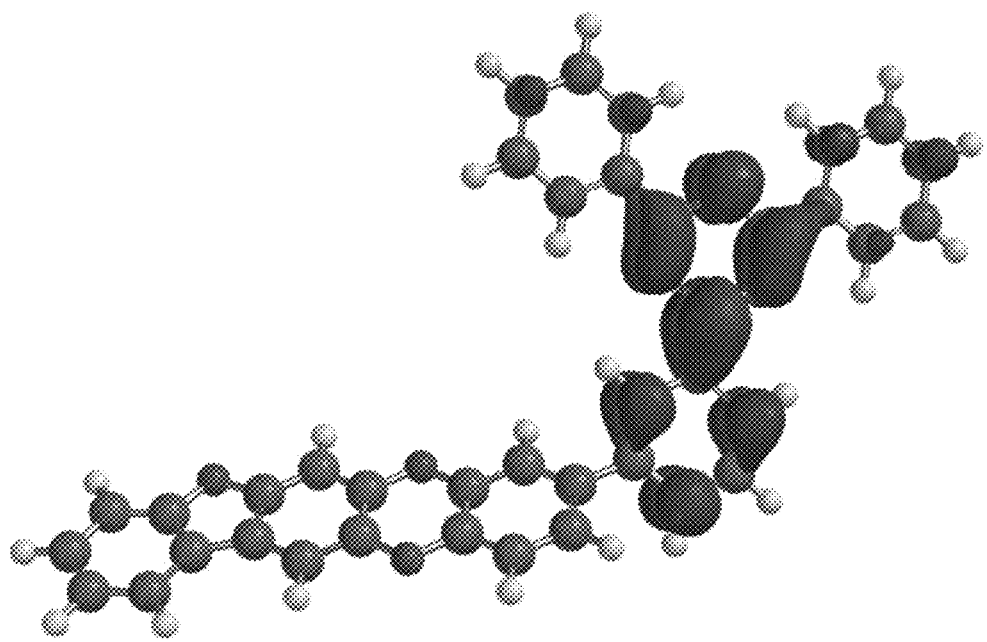
Figure 4A:
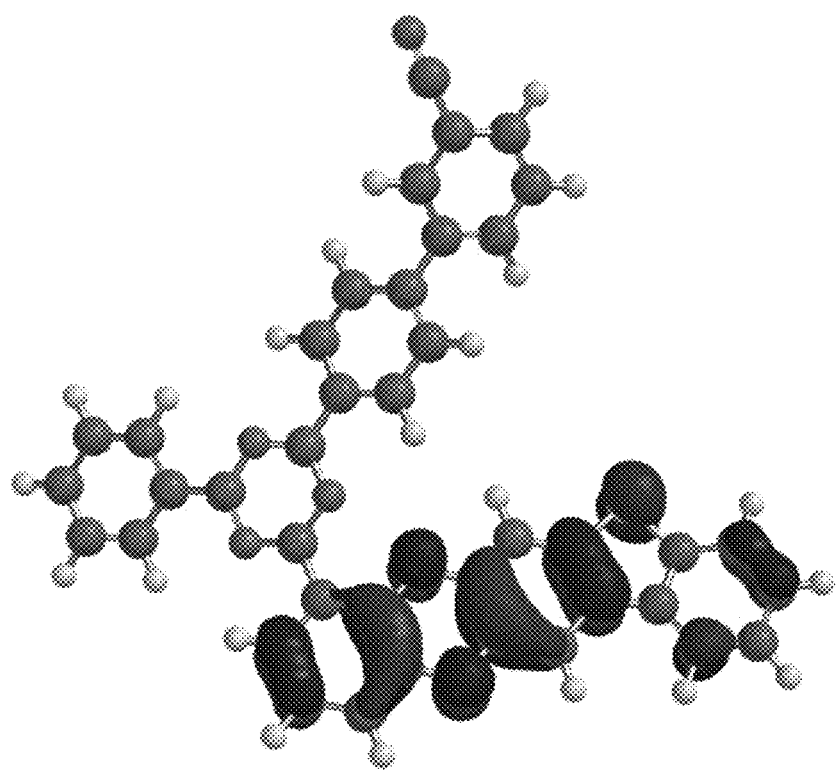
Figure 4B:
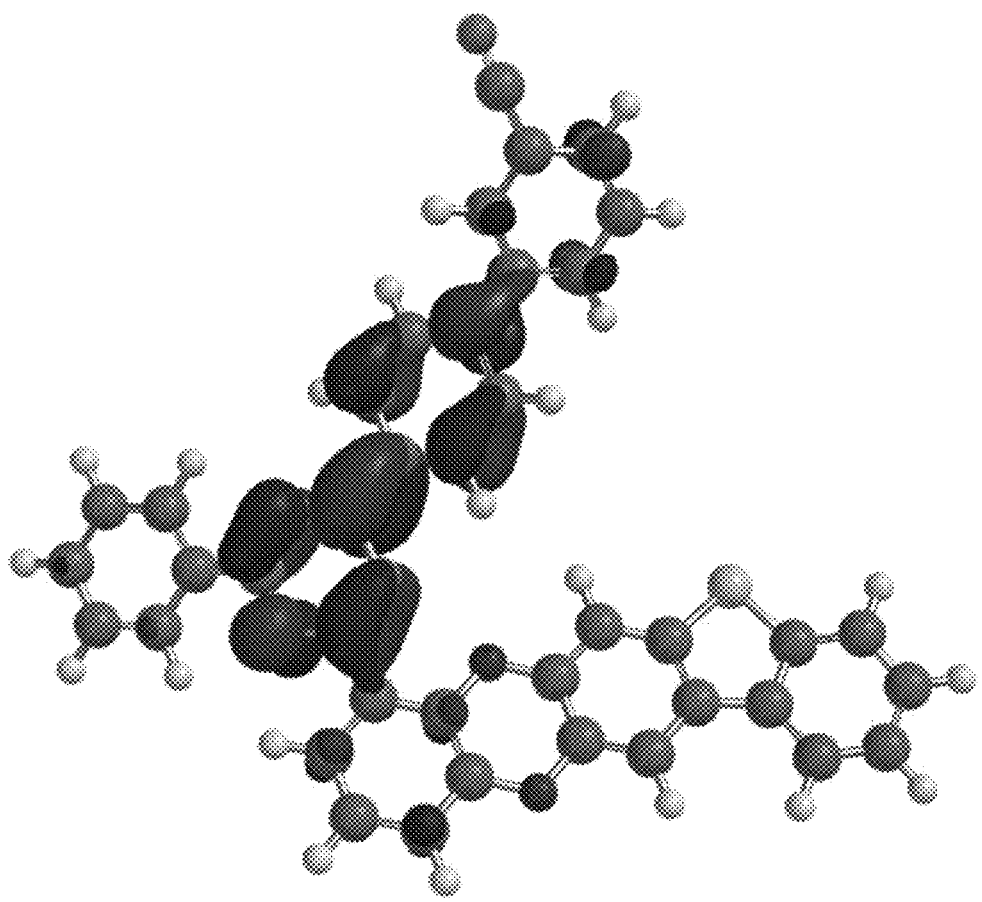

TABLE 1-continued
| Compound | Structure | HOMO distribution | LUMO distribution |
|---|---|---|---|
| dioxin derivative 2 | 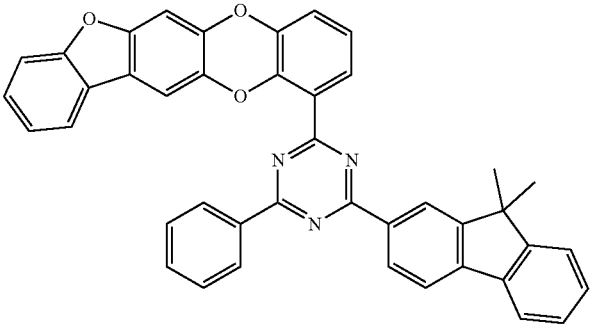 [SMILES: CC1(C)c2ccccc2-c2ccc(-c3nc(-c4ccccc4)nc(-c4cccc5c4Oc4cc6c(cc4O5)oc4ccccc46)n3)cc21] | FIG. 2A | FIG. 2B |
| dioxin derivative 3 | 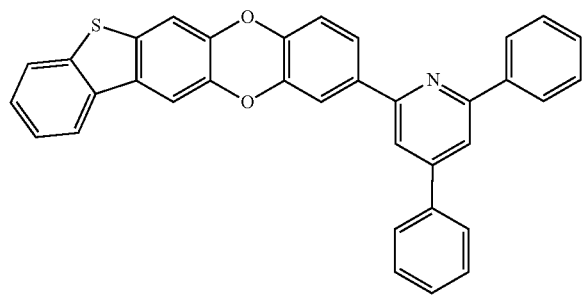 [SMILES: c1ccc(-c2cc(-c3ccccc3)nc(-c3ccc4c(c3)Oc3cc5c(cc3O4)sc3ccccc35)c2)cc1] | FIG. 3A | FIG. 3B |
| dioxin derivative 4 | 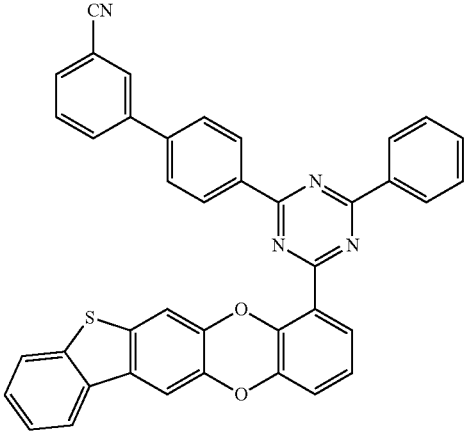 [SMILES: N#Cc1cccc(-c2ccc(-c3nc(-c4ccccc4)nc(-c4cccc5c4Oc4cc6sc7ccccc7c6cc4O5)n3)cc2)c1] | FIG. 4A | FIG. 4B |
In the embodiments, the structure of HAT-CN is
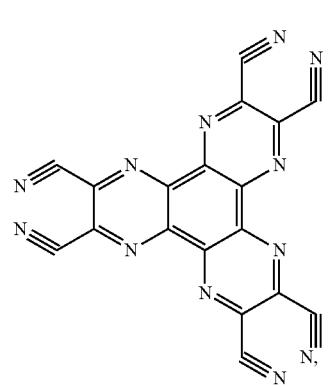 [SMILES: N#Cc1nc2c3nc(C#N)c(C#N)nc3c3nc(C#N)c(C#N)nc3c2nc1C#N]
the structure of NPB is
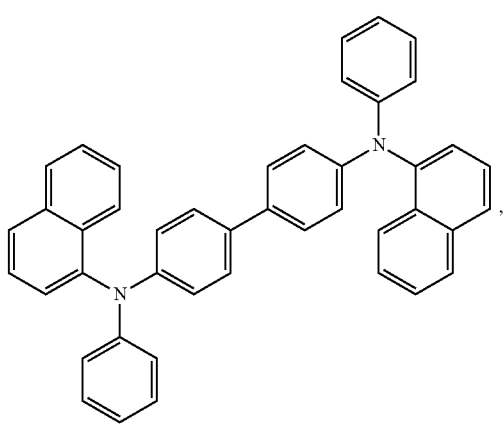 [SMILES: c1ccc(N(c2ccc(-c3ccc(N(c4ccccc4)c4cccc5ccccc45)cc3)cc2)c2cccc3ccccc23)cc1]

the structure of mCBP is

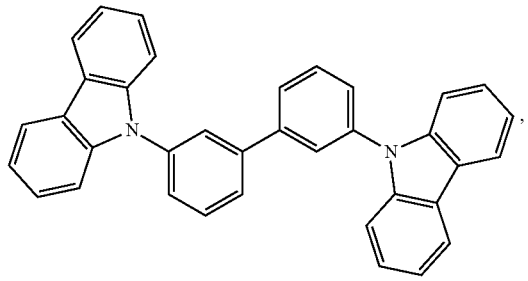 [SMILES: c1cc(-c2cccc(-n3c4ccccc4c4ccccc43)c2)cc(-n2c3ccccc3c3ccccc32)c1]

the structure of BCP is

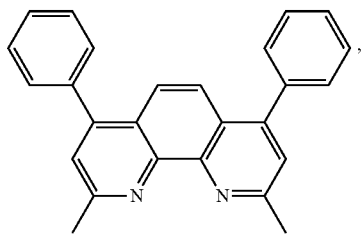 [SMILES: Cc1cc(-c2ccccc2)c2ccc3c(-c4ccccc4)cc(C)nc3c2n1]

the structure of DPVBi is

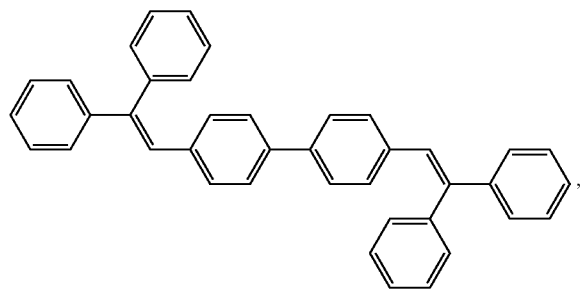 [SMILES: C(=C(c1ccccc1)c1ccccc1)c1ccc(-c2ccc(C=C(c3ccccc3)c3ccccc3)cc2)cc1]

the structure of ADN is

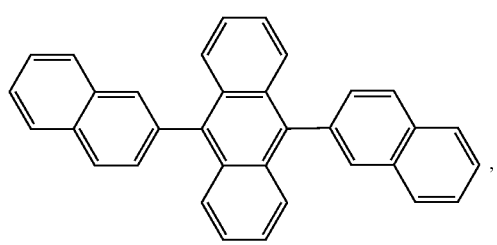 [SMILES: c1ccc2cc(-c3c4ccccc4c(-c4ccc5ccccc5c4)c4ccccc34)ccc2c1]

the structure of Alq$_3$ is

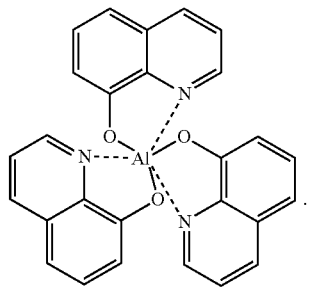

IVL (current, voltage and luminance) of the OLED devices in Embodiments 1-4 and Comparative Example 1 are tested, and the results refer to Table 2. Compared with the Comparative Example 1, the OLED devices in Embodiments 1-4 have advantages of lower driving voltage and higher efficiency, which result from the differences in the material of the ETL.

TABLE 2

|  | Material of ETL | Driving voltage (V) | Emission peak (nm) | Current efficiency (cd/A) |
| --- | --- | --- | --- | --- |
| Embodiment 1 | dioxin derivative 1 | 7.3 | 456 | 7.3 |
| Embodiment 2 | dioxin derivative 2 | 7.0 | 460 | 7.1 |
| Embodiment 3 | dioxin derivative 3 | 7.1 | 458 | 6.9 |
| Embodiment 4 | dioxin derivative 4 | 7.0 | 454 | 7.3 |
| Comparative example 1 | Alq$_3$ | 7.7 | 460 | 5.7 |

The terms "first" and "second" in the specification are only used for descriptive purposes, and should not be understood as indicating or implying relative importance or implicitly indicating a number of technical features indicated. Thus, the features defined with "first" and "second" may explicitly or implicitly include one or more of these features. In the description of the present application, "a plurality of" means two or more than two, unless otherwise specifically defined.

In the description of this specification, description with reference to the terms "an embodiment", "some embodiments", "examples", "specific examples", or "some examples" etc. means that the specific features, structures, materials or characteristics described in an embodiment or example are included in at least one embodiment or example of the present application. In this specification, the schematic representations of the above terms do not necessarily refer to a same embodiment or example. Moreover, the described specific features, structures, materials or characteristics can be combined in any one or more embodiments or examples in a suitable manner. In addition, those skilled in the art can combine or compose the different embodiments or examples and the features of the different embodiments or examples described in this specification without contradicting each other.

Although the embodiments of this application have been shown and described above, it can be understood that the above embodiments are exemplary and should not be construed as limitations of this application. Those skilled in the art can make changes, modifications, substitutions and modifications to the above-mentioned embodiments within the scope of this application.

The invention claimed is:
1. A dioxin derivative selected from group consisting of:
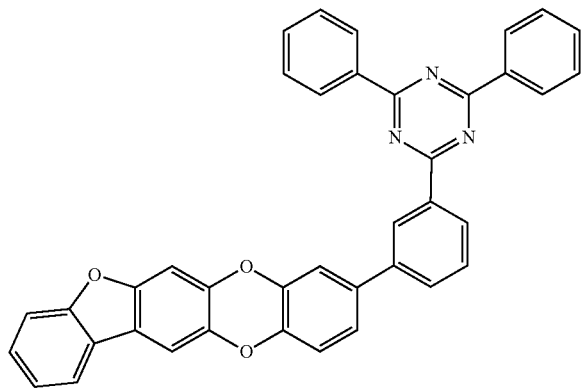
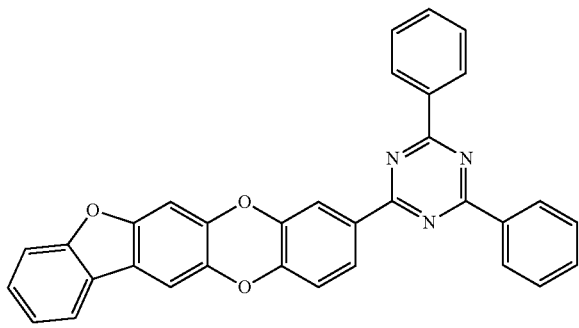
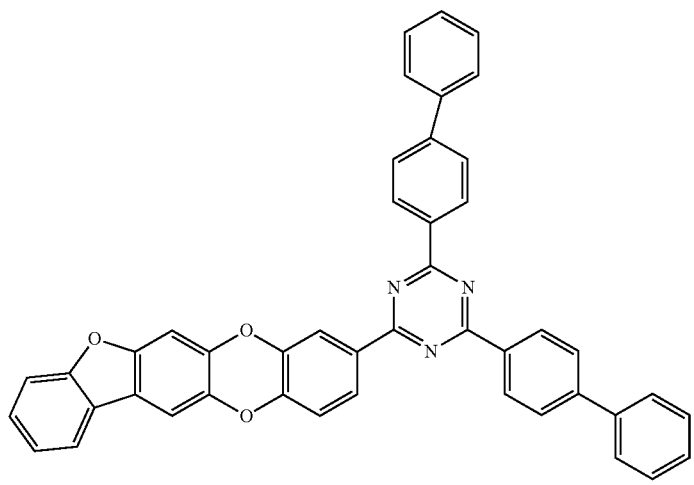
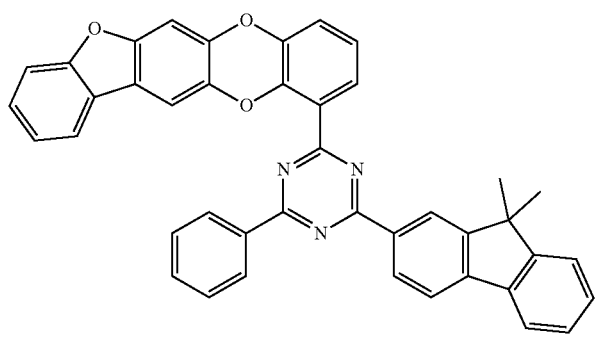
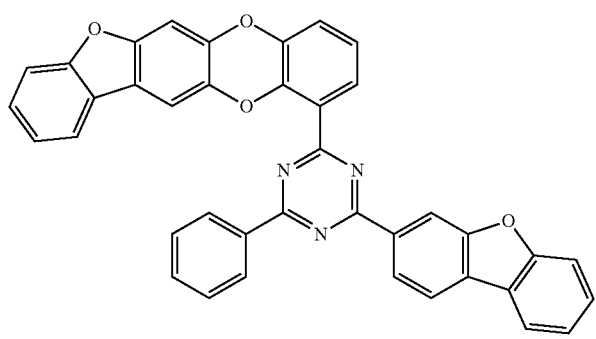

-continued
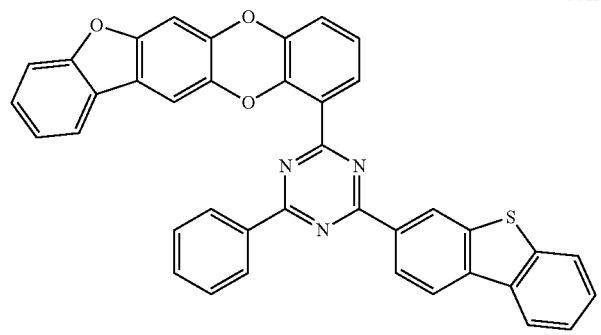
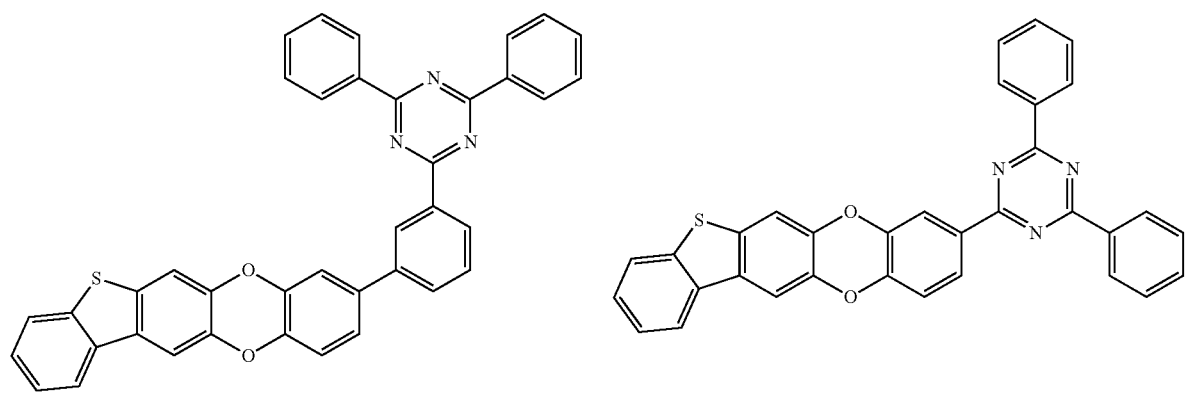
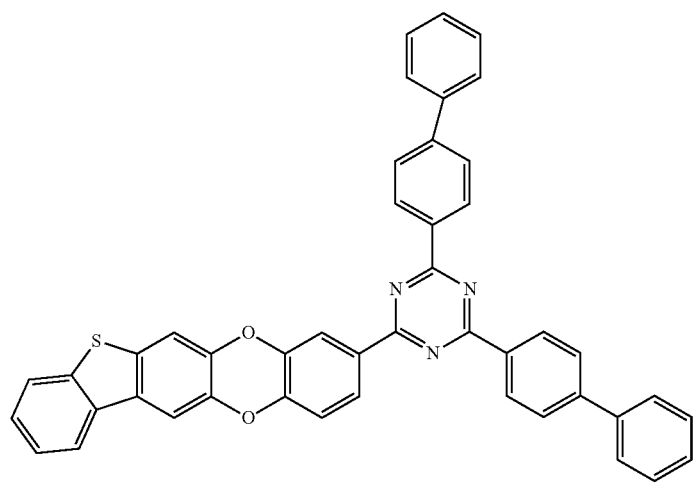
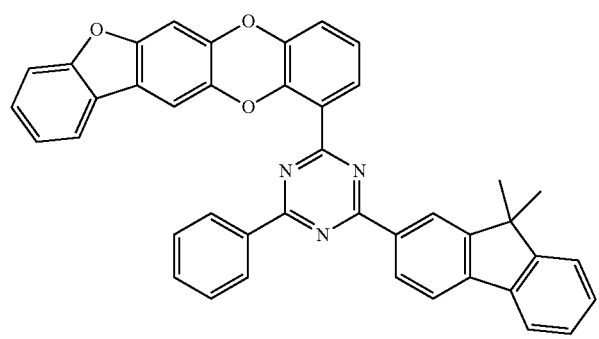

-continued
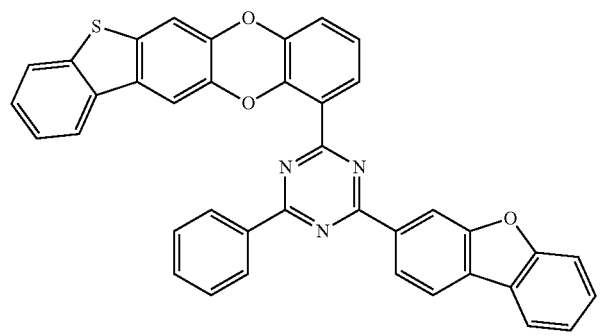
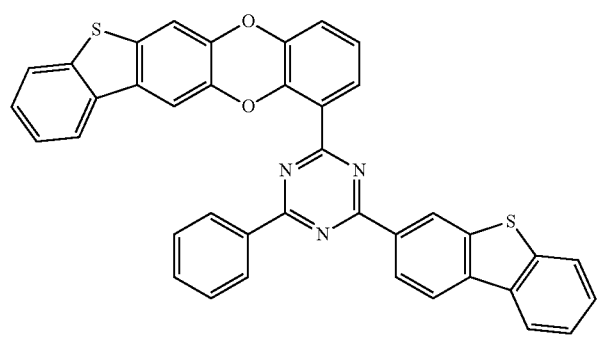
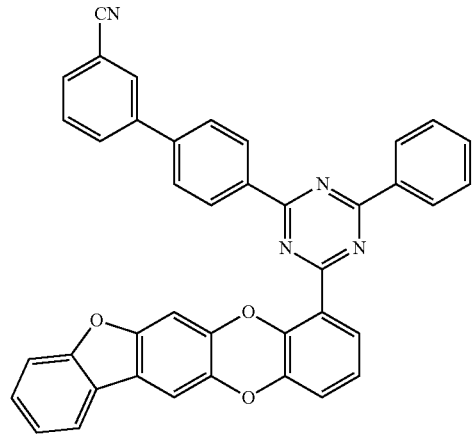
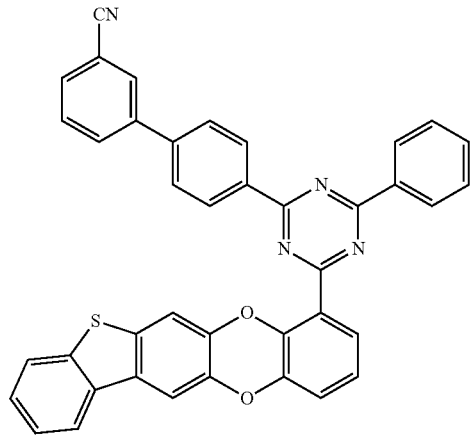
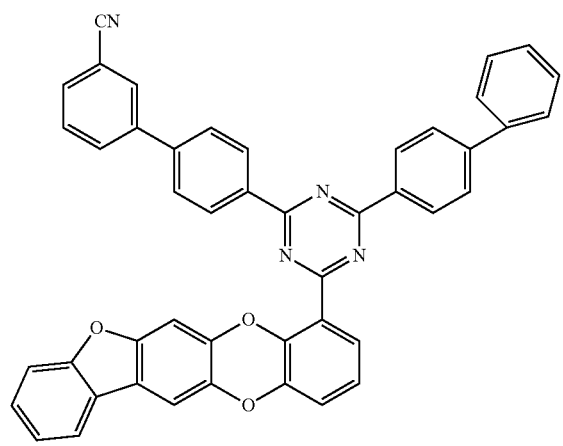
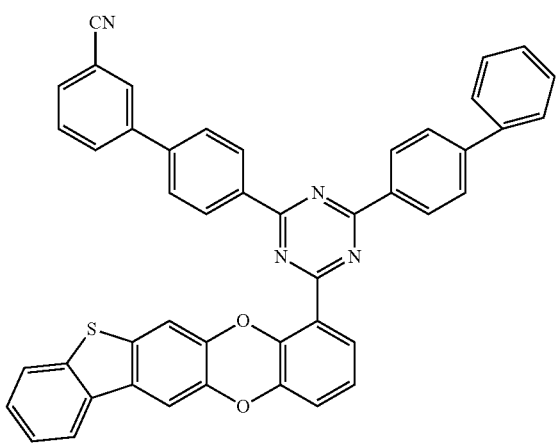

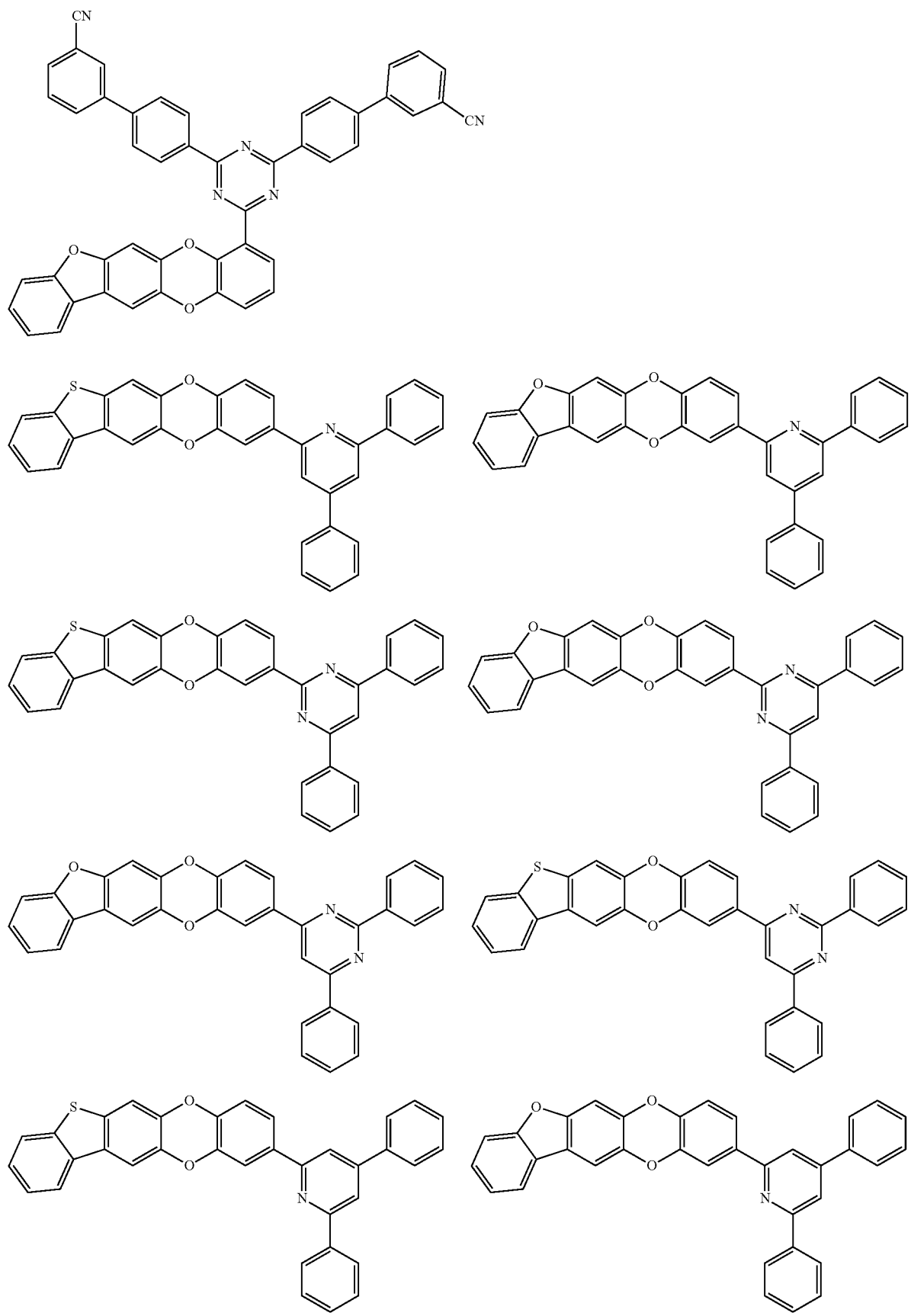

65 66
-continued
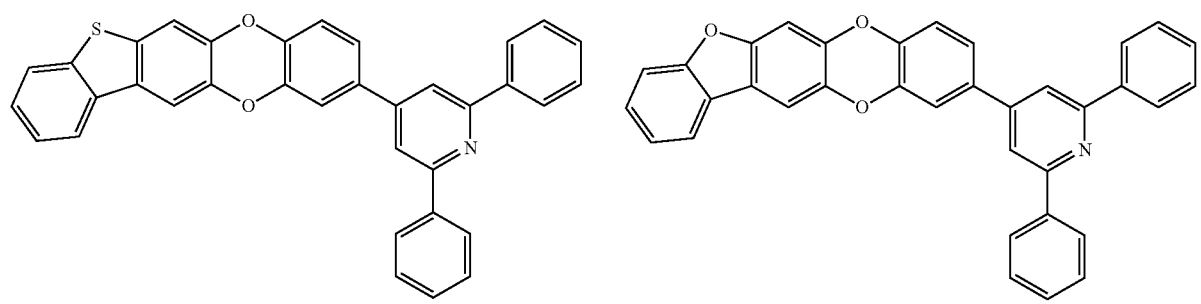
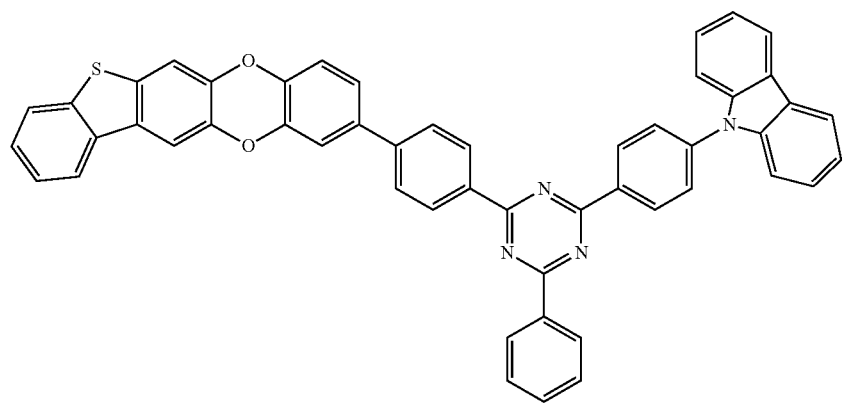
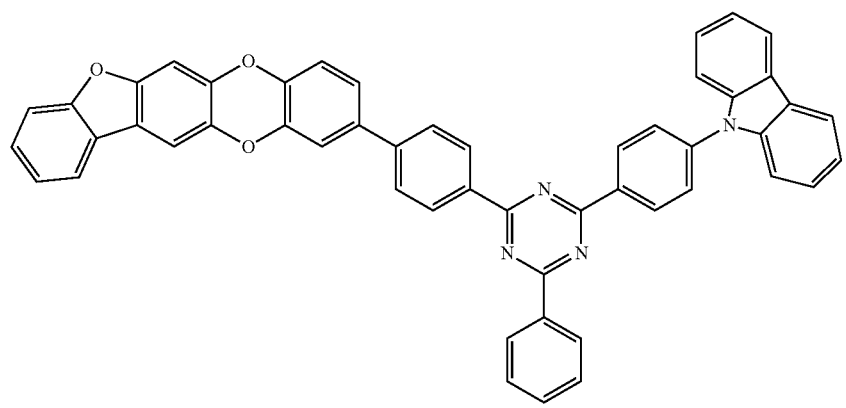
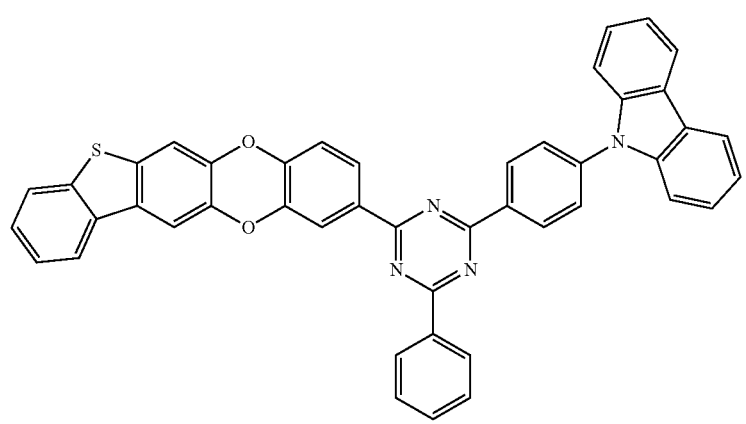

-continued
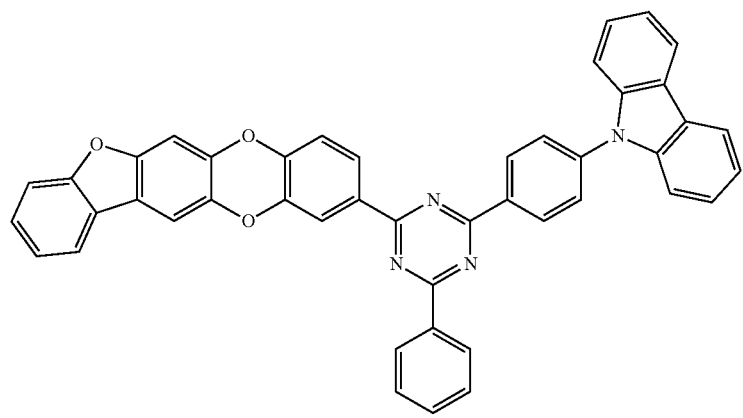
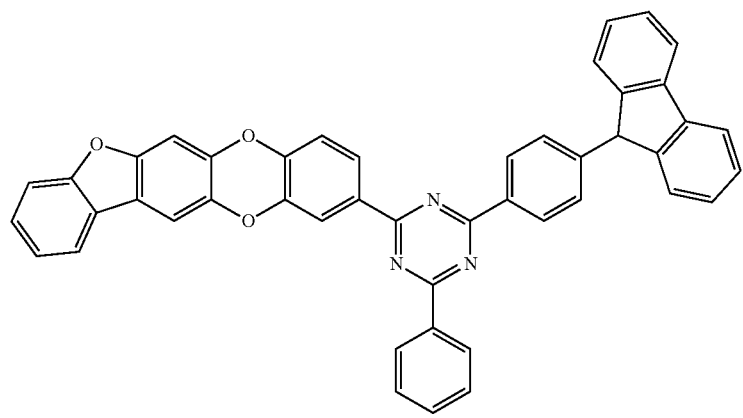
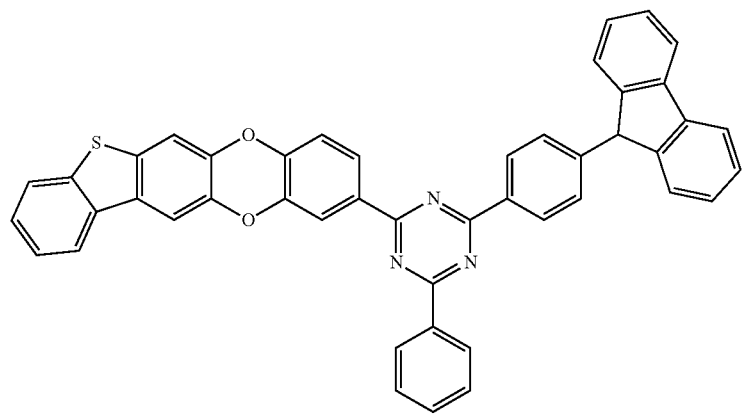
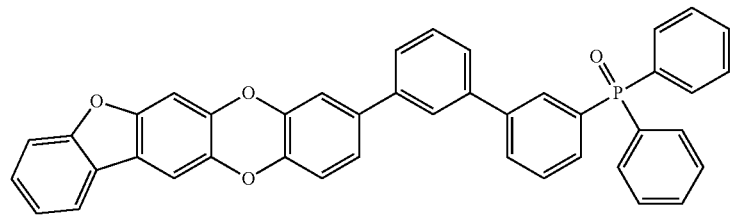

-continued
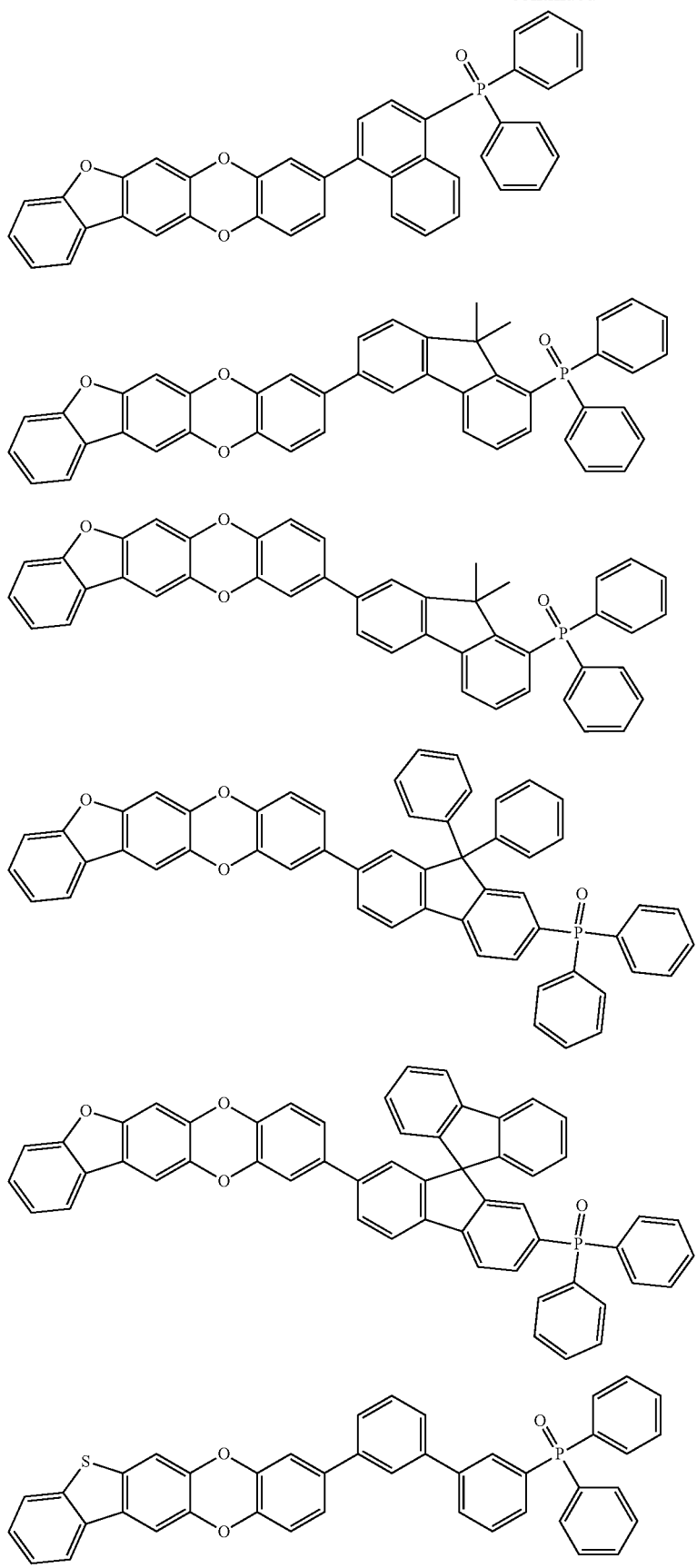

-continued
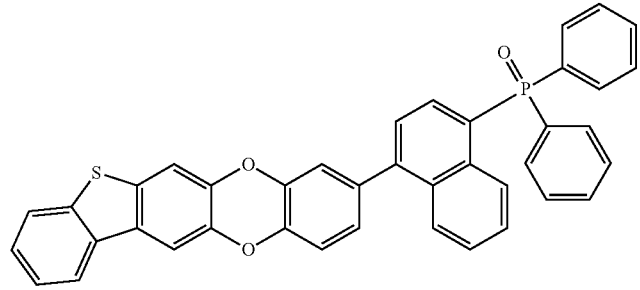
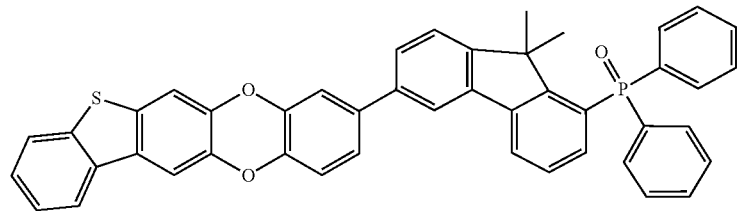
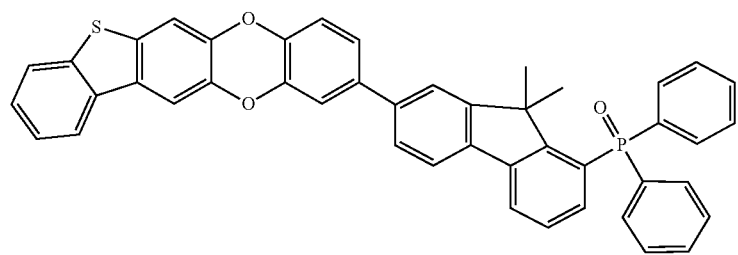
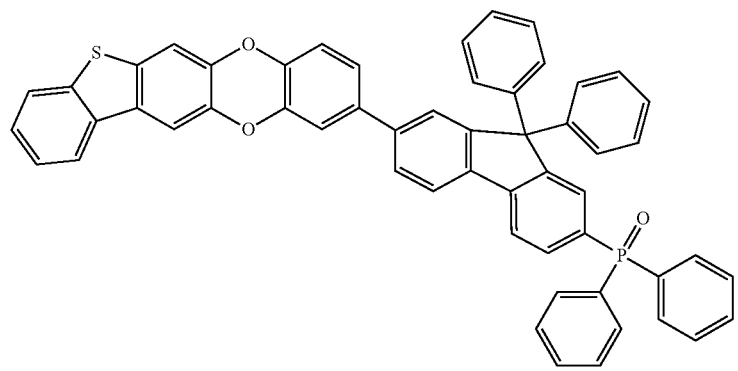
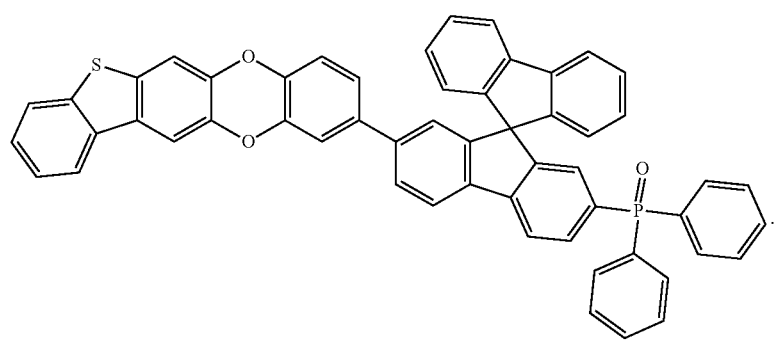

2. A preparation method of a dioxin derivative having a structure represented by

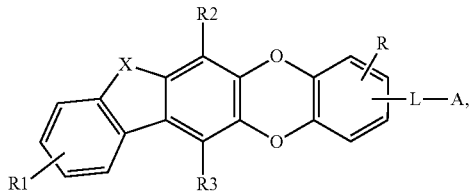

wherein X is O, S or NR;

R, R1, R2 and R3 independently are hydrogen, deuterium, halogen, cyano, nitro, $C_1$-$C_{40}$ alkyl, $C_2$-$C_{40}$ alkenyl, $C_2$-$C_{40}$ alkynyl, $C_3$-$C_{40}$ cycloalkyl, $C_3$-$C_{40}$ heterocycloalkyl, $C_6$-$C_{60}$ aryl, $C_5$-$C_{60}$ heteroaryl, C1-C40 alkoxy, $C_6$-$C_{60}$ aryloxy, $C_3$-$C_{40}$ alkylsilyl, $C_6$-$C_{60}$ arylsilyl, $C_1$-$C_{40}$ alkylboryl, C6-$C_{60}$ arylboryl, $C_6$-$C_{60}$ arylphosphonoyl, $C_6$-$C_{60}$ mono- or di-arylphonphanyl, or $C_6$-$C_{60}$ arylamino;

L represents a direct bond, or L is a substituted or unsubstituted $C_6$-$C_{60}$ arylene, or L is a $C_2$-$C_{60}$ heteroaryl comprising a first heteroatom; and A has a formula of

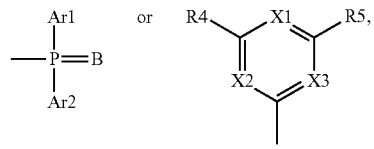

wherein

Ar1 and Ar2 independently are substituted or unsubstituted aryl, phenyl, biphenyl or heterocyclyl comprising a second heteroatom, B is O, S or Se;

X1, X2 and X3 independently are C or N, and at least one of X1, X2 or X3 is N; and R4 and R5 independently are $C_5$-$C_{30}$ aromatic or heteroaromatic group ring;

the method comprising the following steps:

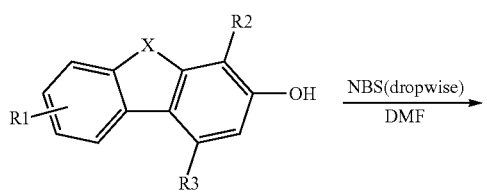 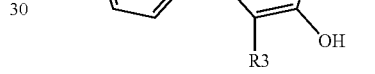

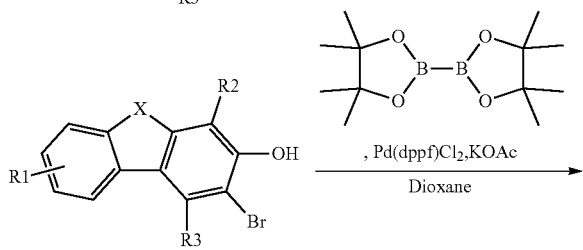

-continued

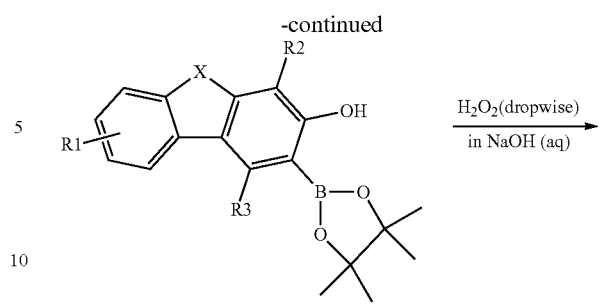

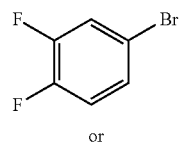

or

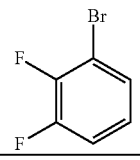

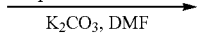

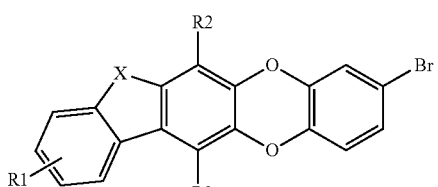

or

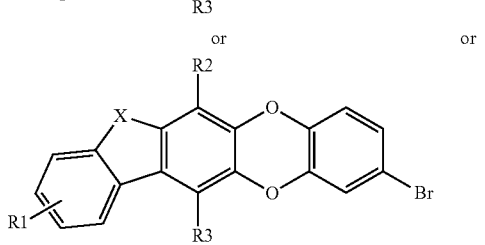

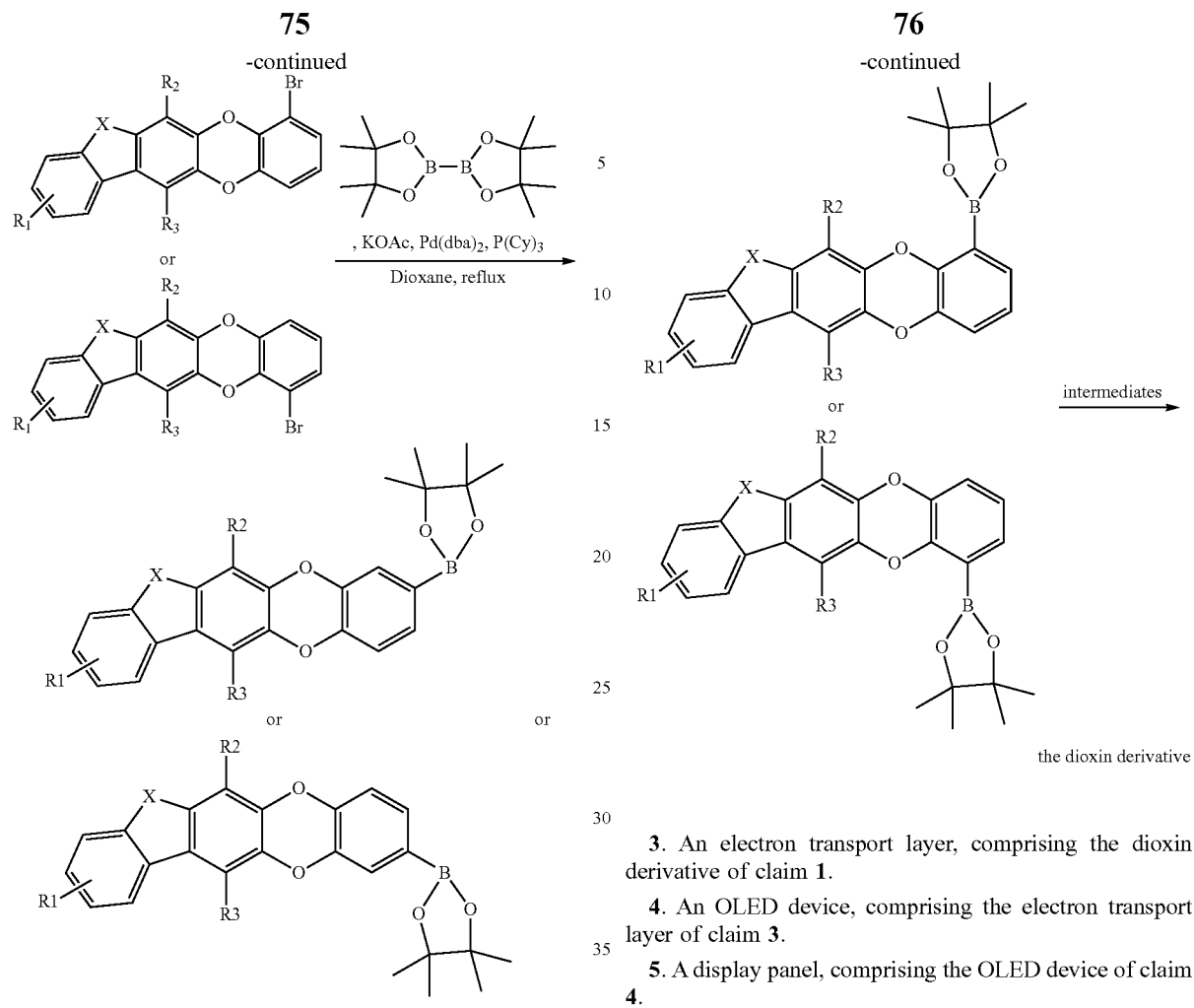
3. An electron transport layer, comprising the dioxin derivative of claim 1.
4. An OLED device, comprising the electron transport layer of claim 3.
5. A display panel, comprising the OLED device of claim 4.
* * * * *